(12) United States Patent
Stankus et al.

(10) Patent No.: US 10,330,694 B2
(45) Date of Patent: Jun. 25, 2019

(54) APPARATUS AND METHOD FOR AUTOMATED SAMPLE PREPARATION AND ADAPTOR FOR USE IN THE APPARATUS

(71) Applicant: DIAGNOSTICS FOR THE REAL WORLD, LTD, Sunnyvale, CA (US)

(72) Inventors: Philip Stankus, Sussex (GB); Paul Duesbury, Cambridgeshire (GB); Torbjorn Blad, Kungsangen (SE); Craig Wisniewski, Cambridgeshire (GB); Jean-Pierre Allain, Cambridgeshire (GB)

(73) Assignee: DIAGNOSTICS FOR THE REAL WORLD, LTD, Sunnyvale, CA (US)

( * ) Notice: Subject to any disclaimer, the term of this patent is extended or adjusted under 35 U.S.C. 154(b) by 0 days.

(21) Appl. No.: 14/777,044

(22) PCT Filed: Mar. 14, 2014

(86) PCT No.: PCT/GB2014/050820
§ 371 (c)(1),
(2) Date: Sep. 15, 2015

(87) PCT Pub. No.: WO2014/140640
PCT Pub. Date: Sep. 18, 2014

(65) Prior Publication Data
US 2016/0033543 A1    Feb. 4, 2016

(30) Foreign Application Priority Data

Mar. 15, 2013 (GB) .................................. 1304797.2

(51) Int. Cl.
*G01N 35/10* (2006.01)
*B01L 3/00* (2006.01)
(Continued)

(52) U.S. Cl.
CPC ........ *G01N 35/1011* (2013.01); *B01L 3/0275* (2013.01); *B01L 3/502* (2013.01);
(Continued)

(58) Field of Classification Search
None
See application file for complete search history.

(56) References Cited

U.S. PATENT DOCUMENTS 5,200,151 A    4/1993 Long
5,310,523 A    5/1994 Smethers et al.
(Continued)

FOREIGN PATENT DOCUMENTS

CN    202803267 U    3/2013
DE    3428953 A1    2/1986
(Continued)

OTHER PUBLICATIONS

Illustra PlasmidePrep Mini Spin Kit, Kit available from GE Healthcare, www.gelifesciences.com/webapp/wcs/stores/servlet/productById/en/GELifeSciences/28904269 and www.gelifesciences.com/gehcls_images/GELS/Related%20Content/Files/1314774443675/litdoc28951561AF_20110831095457.pdf (5 pages) (Jan. 2007).
(Continued)

*Primary Examiner* — Benjamin R Whatley
(74) *Attorney, Agent, or Firm* — Scully Scott Murphy & Presser

(57) ABSTRACT

There is provided an automated biological-sample-processing system comprising a pipette, a column of solid-phase material to which nucleic acid binds, a transport apparatus, an air-piston apparatus and an adaptor for coupling the pipette to the transport apparatus and to the air-piston apparatus, in which the adaptor is removably engageable with the transport apparatus and the air-piston apparatus for movement with the transport apparatus during processing of
(Continued)

the sample, is couplable to the pipette so that the transport apparatus is controllable to position the pipette and so that the air-piston apparatus is controllable to draw a liquid into the pipette and to expel the liquid from the pipette, and is engageable with the column, in which the adaptor comprises a filter for preventing liquid or aerosol transfer between the pipette or column and the air-piston apparatus.

23 Claims, 18 Drawing Sheets

(51) Int. Cl.

| | | |
|---|---|---|
| C12Q 1/68 | (2018.01) | |
| B01L 3/02 | (2006.01) | |
| C12Q 1/70 | (2006.01) | |
| C12N 7/02 | (2006.01) | |
| C12Q 1/6806 | (2018.01) | |
| C12Q 1/686 | (2018.01) | |
| G01N 35/00 | (2006.01) | |
| G01N 35/04 | (2006.01) | |
| G01N 30/46 | (2006.01) | |
| G01N 30/60 | (2006.01) | |
| G01N 30/00 | (2006.01) | |
| G01N 30/88 | (2006.01) | |

(52) U.S. Cl.
CPC ............. *B01L 3/5082* (2013.01); *B01L 3/563* (2013.01); *C12N 7/02* (2013.01); *C12Q 1/6806* (2013.01); *C12Q 1/686* (2013.01); *C12Q 1/703* (2013.01); *G01N 35/10* (2013.01); *B01L 3/5635* (2013.01); *B01L 2200/023* (2013.01); *B01L 2200/025* (2013.01); *B01L 2200/026* (2013.01); *B01L 2200/0668* (2013.01); *B01L 2200/10* (2013.01); *B01L 2200/16* (2013.01); *B01L 2300/046* (2013.01); *B01L 2300/0609* (2013.01); *B01L 2300/0681* (2013.01); *C12N 2740/16011* (2013.01); *C12Q 2545/10* (2013.01); *C12Q 2545/114* (2013.01); *G01N 30/467* (2013.01); *G01N 30/6091* (2013.01); *G01N 2030/009* (2013.01); *G01N 2030/8827* (2013.01); *G01N 2035/00277* (2013.01); *G01N 2035/00475* (2013.01); *G01N 2035/0436* (2013.01); *G01N 2035/103* (2013.01); *G01N 2035/1053* (2013.01)

(56) References Cited

U.S. PATENT DOCUMENTS

| | | | |
|---|---|---|---|
| 5,620,853 | A | 4/1997 | Smethers et al. |
| 2003/0129741 | A1 | 7/2003 | Ramstad |
| 2004/0071602 | A1 | 4/2004 | Yiu |
| 2005/0089450 | A1 | 4/2005 | Al-Mahareeq et al. |
| 2006/0034732 | A1 | 2/2006 | Bargh et al. |
| 2006/0118491 | A1 | 6/2006 | Gjerde et al. |
| 2009/0129978 | A1 | 5/2009 | Wilson et al. |
| 2009/0155123 | A1 | 6/2009 | Williams et al. |
| 2009/0298129 | A1* | 12/2009 | Spence .................. B01L 3/021 435/91.2 |
| 2010/0028204 | A1 | 2/2010 | Lee et al. |
| 2010/0043575 | A1* | 2/2010 | Tajima ................. B01L 3/0275 73/864.11 |
| 2010/0119416 | A1 | 5/2010 | Tajima |
| 2010/0180980 | A1 | 7/2010 | Lee et al. |
| 2012/0270310 | A1 | 10/2012 | Spence et al. |
| 2013/0130369 | A1* | 5/2013 | Wilson ................. B01L 3/5085 435/289.1 |
| 2013/0203089 | A1* | 8/2013 | Wingo .................. B01L 3/0275 435/7.92 |

FOREIGN PATENT DOCUMENTS

| | | | |
|---|---|---|---|
| DE | 10 2004 025 588 A1 | 12/2005 | |
| EP | 0 114 686 A2 | 8/1984 | |
| EP | 0 701 865 A1 | 3/1996 | |
| EP | 0 715 719 B1 | 4/2000 | |
| EP | 2 453 219 A1 | 5/2012 | |
| EP | 2 545 993 A1 | 1/2013 | |
| FR | 2 220 135 A1 | 9/1974 | |
| FR | 2 969 128 A1 | 3/2012 | |
| GB | 1 463 807 A | 2/1977 | |
| GB | 2 443 243 A | 4/2008 | |
| JP | 2011-17568 | 1/2011 | |
| WO | WO 99/46046 A1 | 9/1999 | |
| WO | WO 01/56695 A1 | 8/2001 | |
| WO | WO 2008/012550 A2 | 1/2008 | |
| WO | WO 2009/121034 A2 | 10/2009 | |
| WO | WO 2010/075116 A2 | 7/2010 | |
| WO | WO 2011/012859 A1 | 2/2011 | |
| WO | WO 2012012779 A2 * | 1/2012 | .......... B01L 3/50825 |
| WO | WO 2012/017238 A1 | 2/2012 | |
| WO | WO 2012/040333 A1 | 3/2012 | |
| WO | WO 2012/134440 A1 | 10/2012 | |
| WO | WO 2013/016629 A1 | 1/2013 | |

OTHER PUBLICATIONS

International Search Report dated Jul. 25, 2014 received in International Application No. PCT/GB2014/050820.
European Search Report dated Feb. 11, 2014 received in European Patent Application No. 13 18 8269.
Great Britain Search Report dated Mar. 13, 2014 received in British Application No. GB 1304797.2.
Great Britain Search Report dated Aug. 30, 2013 received in British Application No. GB 1304797.2.

* cited by examiner

APPARATUS AND METHOD FOR AUTOMATED SAMPLE PREPARATION AND ADAPTOR FOR USE IN THE APPARATUS

This invention relates to an apparatus and method for handling biological samples, and in particular for isolation, amplification and testing of nucleic acids.

Methods for isolation of nucleic acids of a quality suitable for downstream applications such as polymerase chain reaction (PCR) and sequencing by adsorption and release from a solid phase are well-established (Vogelstein, B. and Gillespie, D, 1979; PNAS 76, 615). The methods use: (i) a lysis buffer to release nucleic acid from biological samples, (ii) a lysis or a binding buffer to capture nucleic acid to a solid phase, (iii) a wash buffer(s) to wash the captured nucleic acid, and (iv) an elution buffer to release the captured nucleic acid from the solid phase. The quality of nucleic acid isolated using such methods depends on the efficiency of buffer exchange between the lysis, binding, wash and elution steps. Carry-over of lysis, binding or wash buffer into the eluted sample inhibits many downstream applications such as PCR, sequencing and cloning.

To obtain high extraction yield, it is necessary to remove the buffer by centrifugation (for example, Zymo-Spin V, Zymo Research & Fastfilter system, OMEGA bio-tek). Centrifugation is an extremely efficient method of removing buffer from the solid phase, and is particularly advantageous for optimum recovery of elution buffer containing released nucleic acid in the elution step.

The requirement for a centrifugation step to obtain high yield complicates the extraction process. In particular, nucleic acid extraction processes that require a centrifuge cannot be carried out in areas where such equipment is not available, for example in a physician's office or in remote areas. The requirement for a centrifuge is also a particular disadvantage for automated systems because the complexity of such systems is increased. In particular, a robotic arm is required to perform relatively complex actions, such as gripping and movement of sample tubes to transfer them to the centrifuge. This increases the cost and complexity of automated systems, and increases the likelihood of errors occurring.

There is a need, therefore, to provide nucleic acid extraction methods that achieve high yield without requiring a centrifugation step. Co-pending application number GB1204663.7, the contents of which are incorporated herein by reference, describes a process for nucleic acid extraction that does not require centrifugation.

Following extraction of a nucleic acid, it must typically be amplified prior to detection. Amplification is typically mediated by procedures such as (RT)-PCR; strand-displacement amplification (SDA) and transcription-based amplification system TAS (Guatelli et al., Proc. Natl. Acad. Sci. 87: 1874-1878 (1990); Compton, Nature 350: 91-92 (1991)). An essential requirement for assays based on nucleic acid amplification is protection from amplicon contamination, currently solved by working in specialized laboratories using dedicated spaces for sample preparation, amplification and detection. This approach is not applicable for field-testing, near-patient testing and in resource-limited settings.

There is a need to provide simplified nucleic acid extraction, amplification and testing methods that can be more readily automated and implemented inexpensively for field-testing, near-patient testing and in resource-limited settings.

The invention provides systems, adaptors, a method, container, device and kits according to the appended independent claims, to which reference should now be made. Preferred or advantageous features of the invention are defined in dependent sub-claims.

According to a first aspect of the invention, there is provided an automated biological-sample-processing system comprising a pipette, a transport apparatus, an air-piston apparatus and an adaptor for coupling the pipette to the transport apparatus and to the air-piston apparatus, in which the adaptor is removably engageable with the transport apparatus and the air-piston apparatus for movement with the transport apparatus during processing of the sample, and is couplable to the pipette so that the transport apparatus is controllable to position the pipette and so that the air-piston apparatus is controllable to draw a liquid into the pipette and to expel the liquid from the pipette, in which the adaptor comprises a filter for preventing liquid or aerosol transfer between the pipette and the air-piston apparatus.

The system may comprise a column of solid phase material to which a target, such as nucleic acid, binds. The adaptor may be configured to be engageable with the column. In particular the system may be configured to push a sample through the column of solid phase material using the air piston apparatus when the adaptor is engaged with the column and the air-piston apparatus. The air-piston apparatus may be configured to apply a pressure greater that atmospheric pressure to the column of solid phase material to push the sample through the column. In one embodiment, the air-piston apparatus is configured to apply a peak pressure of at least 0.2 bar above atmospheric pressure to the column to push the sample through the column. The air-piston apparatus may be configured to apply a peak pressure of between 0.2 and 2 bar above atmospheric pressure to push the sample through the column. Preferably, the air-piston apparatus is configured to apply a pressure of between 0.4 and 1.5 bar above atmospheric pressure to push the sample through the column. Most preferably the air-piston apparatus is configured to apply a pressure of between 0.7 and 1 bar above atmospheric pressure to push the sample through the column. However, the skilled person may select an appropriate pressure based on the dimensions of the system components and the nature of the sample being processed. The pressure should be sufficient to push the sample through the column within an acceptable time but not so great as to strip the target from the column, damage the column, any filters or the sample itself. The air-piston apparatus may be configured to apply pressure to the column in a continuous fashion or in a stepwise fashion. In one embodiment, the air piston apparatus is configured to halve the air volume above the sample to push the sample through the column. However, greater or lesser volume change may be used.

As used herein, "column of solid phase material" means a generally tubular container which is open at both ends and holds solid phase material between the ends. When a sample is pushed through the column it passes from one end of the tubular container, through the solid phase material to the other end of the tubular container.

The system may advantageously comprise an adaptor lock or striker plate that engages lugs on the adaptor to retain the adaptor in engagement with the transport apparatus and the air-piston apparatus. This ensures that the adaptor remains engaged to the air-piston apparatus even when significant pressure is applied from the air-piston apparatus through the filter in the adaptor.

The filter is advantageously gas permeable, and preferably air permeable, while being substantially impermeable to water droplets. The filter may be formed from any suitable materials, for example sintered polyethylene. The mean pore size of the filter is preferably between 5 and 10 µm. The filter preferably allows an air flow rate through it of between 20 and 200 ml/min, and more preferably between 30 and 110 ml/min. The void volume is preferably between 25% and 50%. The filter preferably has a thickness between 2 mm and 5 mm and more preferably between 3 mm and 4 mm.

The adaptor is advantageously engageable simultaneously with the transport apparatus and the air-piston apparatus. The adaptor is preferably removable from the transport apparatus and the air-piston apparatus for disposal after processing of the biological sample. The adaptor thereby provides a means for coupling pipettes to the air-piston apparatus that prevents contaminants and particulates from being exchanged between the pipette and the air-piston apparatus and, if a new adaptor is used for each sample, prevents contaminants from being passed from one sample to another, while still allowing for accurate volumes to be aspirated and dispensed.

The adaptor may comprise a closure seal for sealing a container containing at least a portion of the sample when the adaptor is removed from the transport apparatus and the air-piston apparatus. This provides a convenient means to contain the processed sample or waste products after the processing sequence has been completed.

The air-piston apparatus or transport apparatus may comprise an open-ended socket for receiving an air-piston-coupling portion of the adaptor. The air-piston-coupling portion of the adaptor may comprise a first circumferential sealing element that provides a gas-tight seal with the open-ended socket. The first circumferential sealing element may be formed of a compliant material. It is advantageous to provide a first sealing element on a disposable adaptor rather than on the air-piston apparatus as any sealing element on the air-piston apparatus would need to be effective for repeated operations and so would require regular maintenance and replacement. This would require a suitably skilled service engineer. However, it is possible, and may be advantageous in some circumstances, for the air-piston apparatus to include a sealing element, such as an o-ring, to provide an additional seal with the adaptor. The sealing element on the air-piston apparatus may seal against and internal surface of the adaptor. Alternatively, or in addition, the adaptor may include more than one first circumferential sealing elements configured to seal with the air-piston apparatus and ensure correct alignment of the adaptor.

The pipette comprises an open-ended cylindrical portion for receiving a pipette-coupling portion of the adaptor, the pipette-coupling portion sealing against a surface of the open-ended cylindrical portion by means of two axially-spaced circumferential sealing elements, such that the pipette is restrained from tilting relative to the adaptor. The open-ended cylindrical portion of the pipette may have a length greater than a distance between the two axially-spaced circumferential sealing elements. The two axially spaced circumferential sealing elements ensure that the pipette is properly aligned relative to the adaptor, without tilting, to ensure that a dispensing end of the pipette is in a known and desired position. The two axially spaced sealing elements also provide sufficient frictional engagement with the pipette to retain the pipette on the adaptor as the transport apparatus moves the adaptor during the processing sequence. The pipette must then be forcibly moved out of engagement with the adaptor when required.

The adaptor may be shaped to allow it to couple to pipettes and other containers of different internal diameters. To allow this, the adaptor may comprise two or more pairs of axially-spaced circumferential sealing elements, wherein each pair of axially-spaced circumferential sealing elements is dimensioned to engage different sized pipettes or containers. The pipette coupling portion of the adaptor then has a stepped profile, with the smallest pair of axially-spaced circumferential sealing elements provided at a lowermost position of the adaptor.

The automated system may further comprise one or more striker plates coupled to the air-piston apparatus. One striker plate may be provided for engagement with a protrusion or recess on the adaptor such that movement of the striker plate relative to the air-piston apparatus engages or disengages the adaptor and the air-piston apparatus. The same or a different striker plate may be operable to engage and disengage the adaptor and the pipette. The one or more striker plates may be automatically controlled, preferably in conjunction with the air-piston apparatus and the transport apparatus. Each of the one or more striker plates may be coupled to and movable by any suitable motive device, such as a servo motor. The use of one or more striker plates with a suitably constructed adaptor allows for full automation of the processing steps, with no human intervention required, in a compact system.

The system may comprise two or more pipettes, and the transport apparatus may be controllable to couple the adaptor with each pipette in turn as required by a sample-processing protocol.

The system may be configured to process only a single sample at one time. However, the automatic system may be configured for processing a plurality of samples simultaneously, with the transport apparatus removably engageable with a corresponding plurality of adaptors for coupling with pipettes for handling liquids for processing each of the plurality of samples. Each sample may be processed in a sequence of steps carried out at different locations spaced along a track, with the plurality of samples processed along a plurality of similar, spaced, parallel tracks. The transport apparatus may be controllable to move pipettes for use in processing each of the plurality of samples simultaneously so that each sample is processed using the same steps at the same time. Alternatively, the system may be configured to process a plurality of samples independently such that processing of different samples may start at different times or may be according to different protocols. The plurality of samples may be any number of samples, such as two, four six or more.

The transport apparatus may be configured to move pipettes and other containers with one degree of freedom, such as vertically up and down, or may be configured to move pipettes and containers with more than one degree of freedom, such as both up and down and horizontally along a track. In the case that the transport apparatus moves pipettes and other containers with only one degree of freedom, the system may be configured to move the track relative to the transport apparatus. For example the tracks may be arranged in a circular shape and may be rotated to bring particular locations along the track into alignment with the transport apparatus.

The system may comprise further sample handling components, such as a syringe. In particular, these components may be configured to allow the adaptor to engage with them and thereby allow the transport apparatus to move them as part of an automatic sample-processing protocol.

The system may further comprise a filter comprising a leukoreduction filter within a filter housing, wherein the filter housing is configured to allow the adaptor to engage with an open end of the filter housing.

Each track may comprise a plurality of recesses for receiving one or more sample handling components, such as pipettes, columns, reagent containers, processing chambers and sample containers. The sample handling components may be held within one or more cartridges. The system may include means for securing the cartridges in the recesses during processing, such as a locking cover plate. The locking cover plate may have apertures corresponding to each of the recesses to allow the adaptor and pipette to access the various sample handling components. Alternatively, in a system in which the cartridges are moved relative to the transport apparatus during processing, a locking tooth or ledge may be used to retain the cartridges when they are aligned with the transport apparatus. This ensures that when the adaptor engages a sample handling component and the transport apparatus moves the sample handling component, the rest of the cartridge remains in the recesses.

The system may further comprise an amplification device configured to amplify a specific, isolated nucleic acid. The amplification device may incorporate an analysis chamber configured to provide an indication of the presence of the specific nucleic acid.

The amplification device may be of the type disclosed in WO2008/012550 and may be operated manually by a user. A manually operated amplification device of this type may include:

a location apparatus having an input port for receiving a sample and one or more reagents;
a processing chamber for receiving the sample having a first opening;
an analysis chamber containing an analyser for analysing the sample after processing, the analysis chamber having a second opening;
the processing chamber being movable relative to the analysis chamber and the input port to enable communication between the processing chamber and the input port when the first opening is disposed in an overlapping relationship with the input port and communication between the processing chamber and the analysis chamber when the first opening is disposed in an overlapping relationship with the second opening; and
a sealing apparatus for sealing the processing chamber and the analysis chamber during processing of the sample.

The amplification device may further include one or more reagent chambers suitable for containing processing reagents. In use, the processing chamber is moved sequentially into communication with the reagent chambers and then into communication with the analysis chamber, to mix the reagents with the sample and so implement a processing protocol or method. The sealing apparatus also seals the reagent chamber or chambers during processing of the sample.

The processing chamber may be pre-loaded with a reagent. Similarly, the analysis chamber and reagent chamber or chambers may be pre-loaded with a reagent. The reagents may be liquid or solid reagents.

In the case of a chamber containing a solid reagent, the chamber may have a side wall extending from a closed end of the chamber, and be preloaded with a solid reagent having a minimum lateral dimension, the chamber having one or more flexible protrusions extending from the side wall towards the closed end, ends of the protrusion(s) being separated from each other or from an opposing side wall of the chamber by a distance sufficiently small to prevent the solid reagent from passing the protrusion(s) and leaving the chamber.

The protrusion(s) are preferably sufficiently flexible to allow the solid reagent to be loaded into the chamber past the protrusions. The protrusion(s) may be in the form of a plurality of spaced fingers.

Alternatively, the amplification device may be configured to be operated automatically by the system. In this case the amplification device may have a similar construction to the manually operated amplification device described above but may be configured to engage with the adaptor.

In one embodiment, the amplification device may comprise:

a location apparatus having an input port for receiving a sample and one or more reagents;
a processing chamber for receiving the sample having a first opening;
an analysis chamber containing an analyser for analysing the sample after processing, the analysis chamber having a second opening;
the processing chamber being movable relative to the analysis chamber and the input port to enable communication between the processing chamber and the input port when the first opening is disposed in an overlapping relationship with the input port and communication between the processing chamber and the analysis chamber when the first opening is disposed in an overlapping relationship with the second opening;
a sealing cap for sealing the input port prior to processing of the sample, the sealing cap being configured to engage the adaptor; and
a sealing apparatus for sealing the processing chamber and the analysis chamber during processing of the sample.

The system may comprise moving means to move the processing chamber relative to the analysis chamber. The moving means may be the transport apparatus or may be a separate component, such as a motor.

The sealing cap may comprise a sealing portion for sealing engagement with the input port and an engagement portion for engagement with the adaptor. The engagement portion may comprise an open-ended cup, with the open end facing away from the sealing portion.

In one embodiment, the amplification device is configured such the processing chamber is rotatable between an initial position in which the first opening is disposed in an overlapping relationship with the input port and a final position in which the first opening is disposed in an overlapping relationship with the second opening. The system may include an engagement element configured to engage a portion of the amplification device, the engagement element coupled to a motor such that operation of the motor causes rotation of the processing chamber relative to the analysis chamber from the initial position to the final position.

The processing chamber may be pre-loaded with a reagent. Similarly, the analysis chamber may be pre-loaded with a reagent.

The system may further comprise a syringe body that is configured to couple to and seal the input port and a plunger that is configured to be received in and seal the syringe. The input port can thus remain sealed from the external environment during an amplification process but further reagents added to the processing chamber from the syringe while maintaining the seal from the external environment. Preferably, the adaptor is engageable with each of the syringe and plunger, simultaneously with the air-piston apparatus, to allow the transport apparatus to move the syringe and plunger during an automated sample-processing protocol.

The system may include including one or more receptacles for receiving sample or reagent containers, wherein the system is configured to maintain the one or more receptacles at one or more predetermined temperatures.

The system may include a programmable controller connected to the transport apparatus and to the air-piston apparatus and optionally to any other controllable component, such as a motor or receptacle, and the controller may be programmed to execute a processing protocol. The system may include a user interface to allow for a user to control the operation of the system. The system may further include user feedback means such as a speaker or visual indicator configured to indicate when a processing protocol, or a sub-routine within a processing protocol, is complete.

The analyser may provide a visual indication of a test result when brought into contact with a processed sample. The system may further comprise an automatic inspection assembly, the automatic inspection assembly comprising an image capture device for capturing an image of the analyser and image processing means connected to the image capture device and configured to determine a test result based on the image captured by the image capture device. The system may further include a light source configured to illuminate the analyser. The analyser may comprise a test strip having a transparent backing layer.

The programmable controller may be programmed to control the operation of the image capture device as well as the air-piston apparatus and the transport apparatus in accordance with a processing protocol.

A system in accordance with the invention may provide a fully automated system for isolating, amplifying and detecting a particular target, such as a nucleic acid. The system may be made inexpensively and does not require a special laboratory environment.

In a second aspect of the invention, there is provided an automated biological-sample-processing system comprising a column of solid phase material to which a target, such as nucleic acid, binds, an air-piston apparatus and an adaptor for coupling the column to the air-piston apparatus, in which the adaptor is removably engageable with the air-piston apparatus, and is couplable to the column so that the air-piston apparatus is controllable to push liquid through the column, in which the adaptor comprises a filter for preventing liquid or aerosol transfer between the column and the air-piston apparatus.

The system of the second aspect may comprise one or more pipettes or sample handling components to which the adaptor is configured to engage. The system may also comprise a transport apparatus configured to engage either the adaptor or sample handling components for moving the adaptor relative to sample handling components to which the adaptor is not engaged.

In a third aspect of the invention, there is provided an adaptor for use in a system in accordance with the first aspect of the invention.

In a fourth aspect of the invention there is provided an adaptor for coupling an air-piston apparatus with a pipette, the adaptor comprising: a first end and a second end and an axially extending bore extending between the first end and the second end; the first end comprising at least one first circumferential sealing element for providing a gas-tight seal with a receiving socket in the air-piston apparatus, the second end comprising a second circumferential sealing element for providing a gas-tight seal with a first pipette or container; and a filter located within the bore between the first and second ends for preventing liquid transfer but allowing gas transfer between the first and second ends of the adaptor.

The adaptor may comprise a third circumferential sealing element for providing an air tight seal with the first pipette or container, the third circumferential sealing element being axially spaced from the second circumferential sealing element. The provision of two axially spaced sealing elements ensures that the first pipette or container is correctly aligned relative to the adaptor.

The second end of the adaptor may further comprises a fourth circumferential seal having a smaller diameter than the second circumferential seal so as to provide an air tight seal with a second pipette or container having a smaller diameter than the first pipette or container. The second end of the adaptor may further comprise a fifth circumferential seal for providing an air tight seal with the second pipette or container, the fifth circumferential seal being axially spaced from the fourth circumferential seal.

The adaptor may have an outer surface and further comprise at least one protrusion or recess formed on the outer surface between the first and second ends, the at least one protrusion or recess allowing an automated biological-sample processing apparatus to move the adaptor into and out of engagement with the air-piston apparatus. Any suitable feature on the adaptor that allows an automated member to engage the adaptor when it is coupled to the air-piston apparatus may be used for this purpose. In a preferred embodiment, the adaptor comprises a first protrusion formed on the outer surface between the first and second ends, the first protrusion allowing an automated biological-sample processing apparatus to move the adaptor into engagement with the air-piston apparatus, and a second protrusion formed on the outer surface between the first and second ends, the second protrusion allowing an automated biological-sample processing apparatus to move the adaptor out of engagement with the air-piston apparatus. The first protrusion may function to allow the adaptor to be locked to the air-piston apparatus so that it cannot be disengaged from the air-piston apparatus unintentionally during a sample processing operation. The first protrusion may also function to limit the position of the adaptor relative to the air-piston apparatus when they are engaged with one another.

The adaptor may further comprise a closure seal between the first and second ends, the closure seal extending in a plane substantially orthogonal to the axial direction and configured to seal an opening of a biological sample container. This provides a convenient means to contain the processed sample or waste products after the sample-processing protocol has been completed.

The adaptor may further comprise a lower protrusion configured to limit the engagement of a pipette with the adaptor.

The adaptor may have a substantially circular cross section. In particular, the first, second and third sealing elements may each have a substantially circular circumference. The closure seal may also have a substantially circular circumference. This ensures that seals can be readily formed by the sealing elements and the closure seal irrespective of orientation. Alternatively, the closure seal may have a substantially non-circular cross section.

In a fifth aspect of the invention, there is provided a cartridge for use in an automated biological-sample-processing system, the cartridge comprising an adaptor in accordance with the third or fourth aspects of the invention, and at least one pipette or column, wherein the pipette or column, or both the pipette and the column, is engageable with the adaptor.

Advantageously, the column is a column of solid phase material to which nucleic acid binds.

Advantageously, the cartridge comprises a plurality of pipettes. The cartridge may also comprise at least one container of a reagent used by the automated biological-sample-processing system.

The cartridge may further comprise a filter comprising a leukoreduction filter within a filter housing, wherein the filter housing is engageable with the adaptor.

The cartridge may further comprise a cartridge housing, the cartridge housing holding the pipette and comprising a clip element that in a retaining position prevents the pipette from being removed from the housing, wherein the adaptor comprises a deflecting portion configured so that when the adaptor engages the pipette the deflecting portion engages the clip element and moves the clip element out of the retaining position to allow the pipette to be removed from the housing.

The cartridge may comprise two or more sections, with one section containing liquid reagents and another section containing dry reagents. Alternatively, liquid reagents may be contained in a separate cartridge to dry reagents.

In one embodiment, there is provided a cartridge for use in an automated biological-sample-processing apparatus, the cartridge comprising an adaptor for coupling an air-piston apparatus with a pipette, the adaptor comprising: a first end and a second end and an axially extending bore extending between the first end and the second end; the first end comprising at least one first circumferential seal for providing a gas-tight seal with a receiving aperture in the air-piston apparatus, the second end comprising a second circumferential seal suitable for providing a gas-tight seal with a first pipette or container; and a filter located within the bore between the first and second ends for preventing liquid transfer but allowing gas transfer between the first and second ends, and a biological sample container, the adaptor comprising a closure seal between the first and second ends, the closure seal extending in a plane substantially orthogonal to the axial direction and configured to seal an opening of the biological sample container.

In sixth aspect of the invention, there is provided a method for automated processing of a biological sample, comprising the step of providing an adaptor to couple a pipette to a transport apparatus and an air-piston apparatus, the adaptor being removably engageable with the transport apparatus and the air-piston apparatus, and providing a filter in the adaptor for preventing liquid or aerosol transfer between the pipette and the air-piston apparatus.

Preferably, the filter is gas permeable but substantially impermeable to water droplets. The method may comprise coupling the adaptor to a pipette, moving and operating the pipette using the transport apparatus and the air-piston apparatus, uncoupling the adaptor from the pipette, coupling the adaptor with a column of solid phase material to which nucleic acid selectively binds and pushing a sample through the column of solid phase material using the air-piston apparatus. Preferably, the method comprises applying a pressure of above atmospheric pressure to the column to push the sample through the column. The method may comprise applying a peak pressure of at least 0.2 bar above atmospheric pressure to the column. The method preferably comprises applying a peak pressure of less than 2 bar above atmospheric pressure to the column. More preferably, the method comprises applying a peak pressure of between 0.4 and 1.5 bar above atmospheric pressure to the column. Most preferably, the method comprises applying a peak pressure of between 0.7 and 1 bar above atmospheric pressure to the column. The method may comprise substantially halving the volume of air contained between the sample and the air piston apparatus to apply pressure to the sample. However, greater or lesser reduction on air volume may be used. The method may further comprise the step of pushing the biological sample through a leukoreduction filter using the air-piston apparatus.

The method may further comprise the step of providing an amplification device configured to amplify a specific nucleic acid, wherein the adaptor is removably engageable with the amplification device.

In a seventh aspect of the invention, there is provided a container for use in an automatic biological-sample-processing system, the container having a side wall extending from a closed end of the container, and being preloaded with a solid reagent having a minimum lateral dimension, the container having one or more flexible protrusions extending from the side wall towards the closed end, ends of the protrusion(s) being separated from each other or from an opposing side wall of the container by a distance sufficiently small to prevent the solid reagent from passing the protrusion(s) and leaving the container.

The protrusion(s) are preferably sufficiently flexible to allow the solid reagent to be loaded into the container past the protrusions. The protrusion(s) may be in the form of a plurality of spaced fingers.

The protrusions may be provided on an insert component separate to the container. The insert component may comprise a collar and one or more flexible protrusions extending from the collar, wherein the collar is configured to engage a side wall of the container.

In an eighth aspect of the invention, there is provided an insert component comprising a collar and one or more flexible protrusions extending from the collar, wherein the collar is configured to engage an internal side wall of a reagent container.

This type of insert component allows a solid reagent to be loaded into a container, past the flexible protrusions but prevents the solid reagent from subsequently leaving the container. As an alternative, an insert component consisting simply of a annular collar may be provided to prevent escape of a solid reagent but allow a diluents to be introduced into the container to dissolve the solid reagent. This type of insert component must be loaded into a container subsequent to the loading of the solid reagent.

In a ninth aspect of the invention there is provided a device for processing and analysis of a sample, comprising:
  a location apparatus having an input port for receiving a sample and one or more reagents;
  a processing chamber for receiving the sample having a first opening;
  an analysis chamber containing an analyser for analysing the sample after processing, the analysis chamber having a second opening;
  the processing chamber being movable relative to the analysis chamber and the input port to enable communication between the processing chamber and the input port when the first opening is disposed in an overlapping relationship with the input port and communication between the processing chamber and the analysis chamber when the first opening is disposed in an overlapping relationship with the second opening;

a sealing cap for sealing the input port prior to processing of the sample; and a sealing apparatus for sealing the processing chamber and the analysis chamber during processing of the sample.

The device for processing and analysis of a sample may be an amplification device configured to allow for the amplification of a specific target, such as a nucleic acid.

The sealing cap may comprise a sealing portion for sealing engagement with the input port and an engagement portion for engagement with cap removing component. The engagement portion may comprise an open-ended cup, with the open end facing away from the sealing portion. The open ended cup may be configured to engage with an adaptor of the type described in the second and third aspects of the invention.

The processing chamber may be pre-loaded with a reagent prior to reception of a sample. The reagent may be a solid reagent, such as freeze dried reagent.

The processing chamber may have a side wall extending from a closed end of the processing chamber, and may be preloaded with a solid reagent having a minimum lateral dimension, the processing chamber having one or more flexible protrusions extending from the side wall towards the closed end, ends of the protrusion(s) being separated from each other or from an opposing side wall of the processing chamber by a distance sufficiently small to prevent the solid reagent from passing the protrusion(s) and leaving the processing chamber.

The device for processing and analysis of a sample may be non-reusable. In this case, the device may be constructed from cheap materials and simply thrown away after use. This may be an advantage when the device is used in regions of the world with limited resources, for example if the device used for medical testing in third world countries.

Preferably, during use, gravity acts to introduce the analyser into the processing chamber. This reduces the required mechanical components in the device and simplifies its use. The analyser may be a test strip or dipstick providing a visually readable result. The analysis chamber or processing chamber may have a wall that is substantially transparent to allow the test strip to be viewed.

The device may comprise a top portion and a bottom portion movable relative to one another, wherein the processing chamber is formed in the bottom portion, and the input port and the analysis chamber are formed in the top portion. The sealing apparatus may be disposed between the top portion and the bottom portion to seal the processing chamber and the analysis chamber during processing of the sample. The top portion and the bottom portion may each be formed as a single piece from a mouldable plastics material. The sealing apparatus may be formed from a compliant material.

The top portion may be rotatable relative to the bottom portion or alternatively may be translatable relative to the bottom portion. In one embodiment, the device is configured such the processing chamber is rotatable relative to the analysis chamber between an initial position in which the first opening is disposed in an overlapping relationship with the input port and a final position in which the first opening is disposed in an overlapping relationship with the second opening. The device may include a ratchet mechanism to prevent movement of the processing chamber out of its final position in which the first opening is disposed in an overlapping relationship with the second opening.

The device may comprise one or more protrusions or recesses formed on the upper portion configured for engagement with an automatic movement apparatus The device may further comprise one or more protrusions or recesses formed on the lower portion configured for engagement with an automatic movement apparatus. The processing chamber may be configured for engagement with an automatic movement apparatus.

In a tenth aspect of the invention, there is provided a kit, the kit comprising a device in accordance with the ninth aspect of invention and a syringe, wherein the syringe is configured to be received in the input port of the device and thereby seal the input port.

The syringe may include a sealing element configured to seal an output opening of the syringe, the syringe and sealing element configured to allow the sealing element to pass through the output port or to allow the sealing element to rupture on application of sufficient pressure on the sealing element. The kit may comprise a plunger configured to engage and seal the syringe. Depression of the plunger into the syringe may operate to apply pressure to the sealing element. This arrangement allows the syringe to seal the input port of the device following the introduction of the sample into the device but prior to the operation of the syringe to introduce a further reagent into the device. For example, the syringe may seal the input port, and thereby seal the processing chamber during an amplification process. The syringe may then be used to introduce a detection reagent into the processing chamber while still maintaining the processing chamber sealed from the external environment. The sealing element may be a bead, formed for example from glass. The syringe may be formed from a plastic material that deforms and allows the bead to pass into the processing chamber on depression of the plunger received within the body of the syringe. Alternatively the sealing element may be a rupturable film.

In an eleventh aspect of the invention, there is provided a kit comprising: an adaptor in accordance with the third or fourth aspects of the invention and one or more pipettes or columns that are configured to engage with the adaptor. In particular the adaptor may comprise: a first end and a second end and an axially extending bore extending between the first end and the second end; the first end comprising at least one first circumferential seal for providing a gas-tight seal with a receiving aperture in an air-piston apparatus, the second end comprising a second circumferential seal suitable for providing a gas-tight seal with a first pipette or column; and a filter located within the bore between the first and second ends for preventing liquid transfer but allowing gas transfer between the first and second ends. The kit may further comprise one or more containers containing one or more reagents.

The kit may comprise a column of solid phase material to which nucleic acid binds, the column being engageable with the adaptor. The kit may comprise a filter comprising a leukoreduction filter within a filter housing, wherein the filter housing is engageable with the adaptor.

The kit may further include an amplification device of the type described with reference to the ninth aspect of the invention. The amplification device may be manually or automatically operable. The amplification device may be configured to engage with the adaptor.

In a preferred embodiment, the kit may comprise: an adaptor for coupling an air-piston apparatus with a pipette, the adaptor comprising: a first end and a second end and an axially extending bore extending between the first end and the second end; the first end comprising at least one first circumferential seal for providing a gas-tight seal with a receiving aperture in the air-piston apparatus, the second end comprising a second circumferential seal suitable for providing a gas-tight seal with a first pipette or container; and a filter located within the bore between the first and second ends for preventing liquid transfer but allowing gas transfer between the first and second ends,
one or more pipettes that are configured to engage with the adaptor, and
an amplification device configured to amplify a specific, isolated nucleic acid, wherein the amplification device comprises:
a location apparatus having an input port for receiving a sample and one or more reagents;
a processing chamber for receiving the sample having a first opening;
an analysis chamber containing an analyser for analysing the sample after processing, the analysis chamber having a second opening;
the processing chamber being movable relative to the analysis chamber and the input port to enable communication between the processing chamber and the input port when the first opening is disposed in an overlapping relationship with the input port and communication between the processing chamber and the analysis chamber when the first opening is disposed in an overlapping relationship with the second opening;
a sealing cap for sealing the input port prior to processing of the sample, the sealing cap being configured to engage the adaptor; and
a sealing apparatus for sealing the processing chamber and the analysis chamber during processing of the sample.

The kit may further comprise a syringe and a plunger, each configured to engage with the adaptor, the plunger configured to be received in the syringe, the syringe configured to sealingly engage with the amplification device.

The kit may further comprise a container in accordance with the seventh aspect of the invention.

In a twelfth aspect of the invention, there is provided a kit comprising one or more cartridges, the cartridges containing a column of solid phase material to which nucleic acid binds and one or more pipettes or one or more reagent containers containing reagents, or both one or more pipettes and one or more reagent containers. The kit may comprise at least one reagent container containing a dry reagent and at least one container comprising a wet reagent or diluent. The kit may further comprise a sample container configured to receive a biological sample. The kit may comprise a filter comprising a leukoreduction filter within a filter housing.

A further aspect of the invention relates to testing of HIV viral load (VL). HIV VL testing traditionally employs plasma as the sample medium because plasma is devoid of CD4+ cells that carry proviral DNA and platelets (which carry surface-bound HIV). However, the disadvantages of using plasma include the requirement for a trained phlebotomist and centrifugal equipment. Neither of these may be available, particularly where it is desired to carry out the test in resource-limited settings, such as at a remote location or in a physician's office.

The Applicant has appreciated that these disadvantages may be overcome by using leukocyte depleted blood for HIV viral load testing. Leukocyte depleted blood is depleted of CD4 positive cells and monocytes which contain HIV DNA, and so may be used directly to detect HIV RNA as a measurement of HIV viral load.

According to the invention there is provided a method of testing HIV viral load, which comprises detecting HIV viral RNA in a sample of leukocyte depleted blood.

A sample of leukocyte depleted blood may be prepared by depleting a whole blood sample of leukocytes.

Leukocyte depleted blood can readily be prepared by filtering whole blood through a leukoreduction filter. Filters currently in production include Leucoflex MTLI (Macopharma), Leucoflex LXT (Macopharma), Composelect WB (Fresenius), Sepacell RZ-2000F (Asahi KASEI), Imuflex WB-SP (Terumo), Leukotrap RC-PC (Haemonetics) and Leukotrap PL (Haemonetics). All of the these filters remove leukocytes and (at least some) platelets from whole blood. The amount of erythrocytes retained is ~6%.

A sample of whole blood may be collected, for example, from a finger prick, and then processed by passing the sample through a leukoreduction filter. If the sample volume is small (typically ~150 ul from a finger prick), it may be necessary to dilute the sample with an isotonic solution, or to wash the filter with isotonic solution.

Conventional leukoreduction filters are dependent on gravity alone to cause blood to pass through the filter. However, it may be necessary to apply a pressure differential across the filter to cause the sample to pass through the filter, for example for small sample sizes.

According to a preferred embodiment of the invention, the leukoreduction filter may be disposed within a filter housing that can engage with an air piston apparatus via the adaptor of the second or third aspect of the invention.

It will be appreciated that a whole blood sample can be filtered through the leukoreduction filter prior to subsequent sample processing steps using the system of the first aspect of the invention.

It should be clear that features of the invention described in relation to one aspect may equally be applied to other aspects of the invention. In particular, it should be clear that the features of the components, such as adaptors, containers and devices described in one aspect of the invention may equally be applied to corresponding components described in other aspects of the invention.

Preferred embodiments of the invention are now described, by way of example only, with reference to the accompanying drawings, in which:

FIG. 5b is a cross section view of the adaptor of FIG. 4a;

FIG. 8b illustrates the insert of FIG. 8a;

Figure 1:
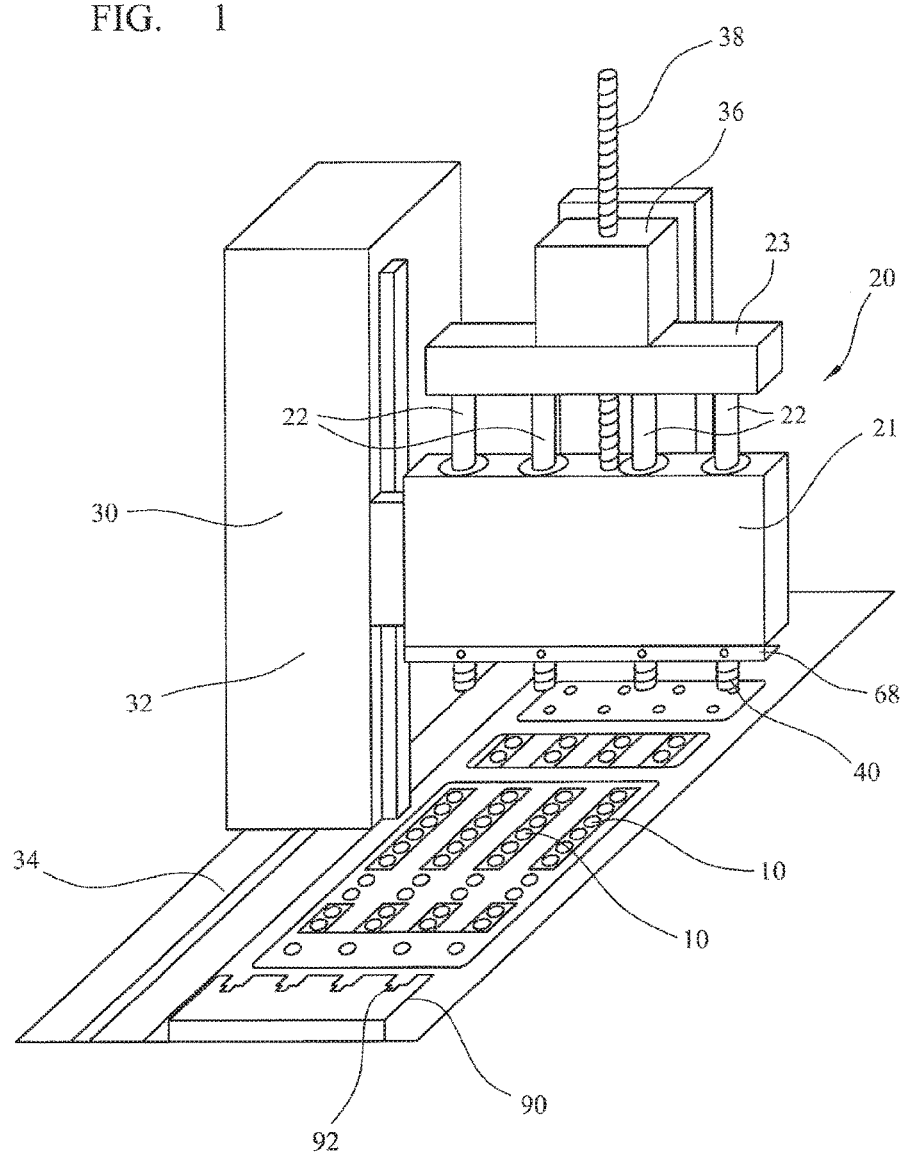
FIG. 1 is a perspective view of an apparatus for sample preparation in accordance with the invention.
Figure 2:
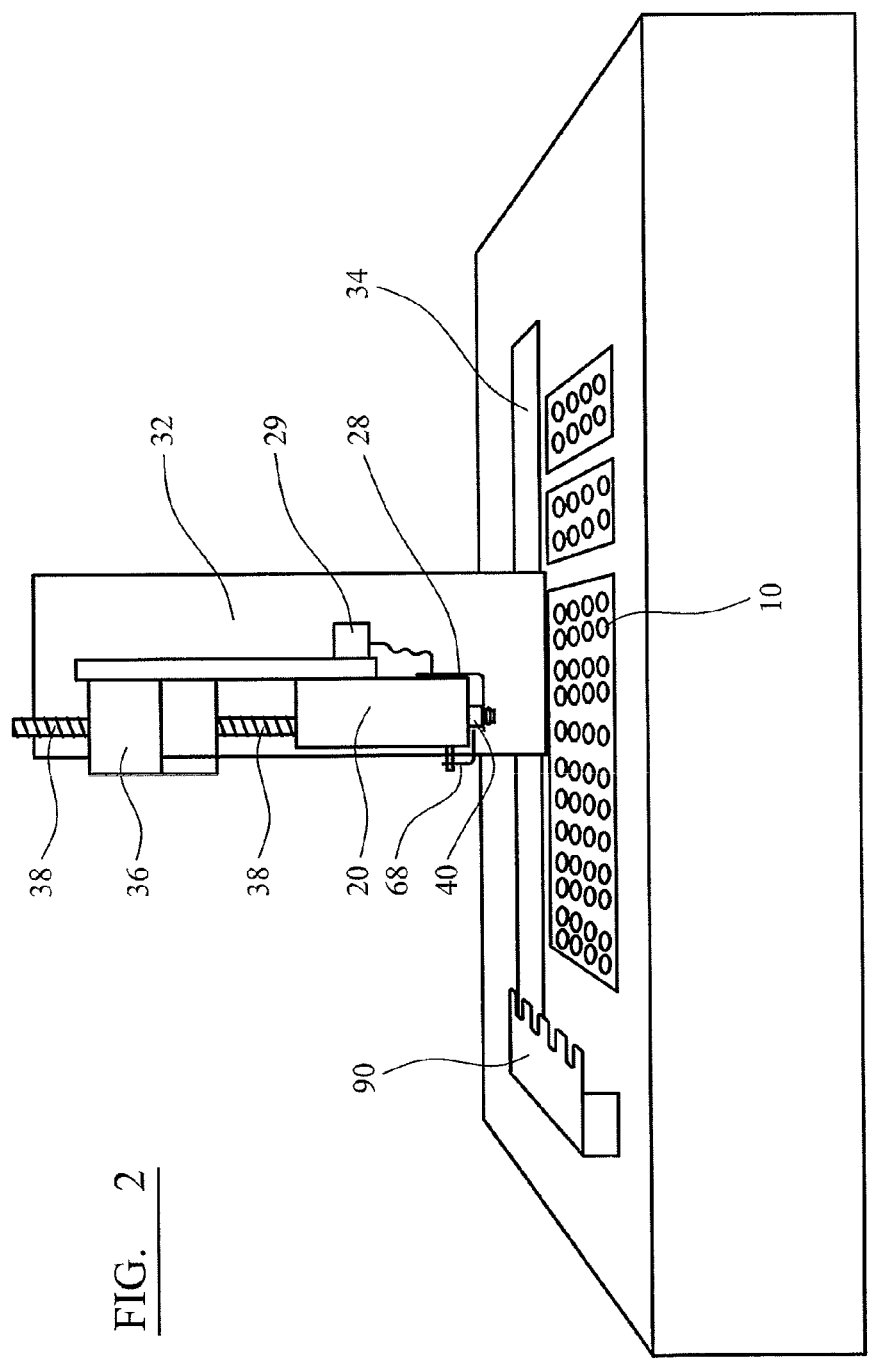
FIG. 2 is a side view of the apparatus of FIG. 1.
Figure 9A:
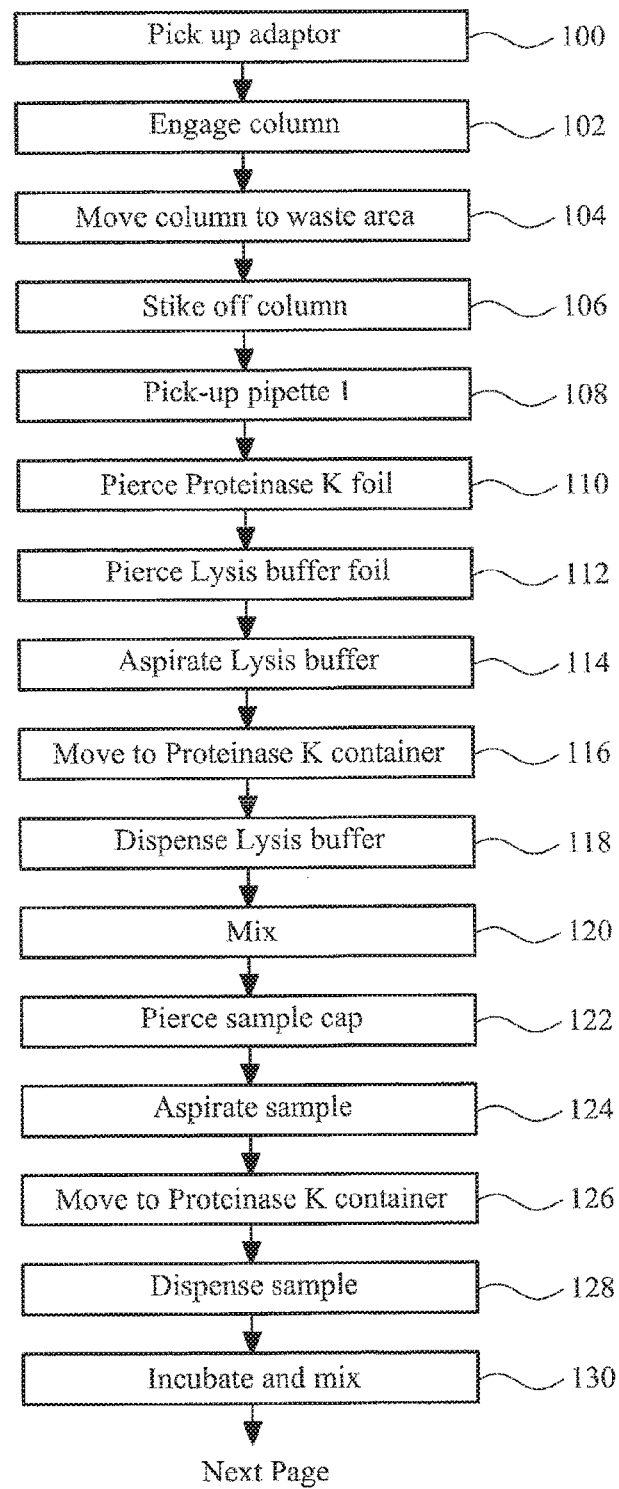
Figure 9B:
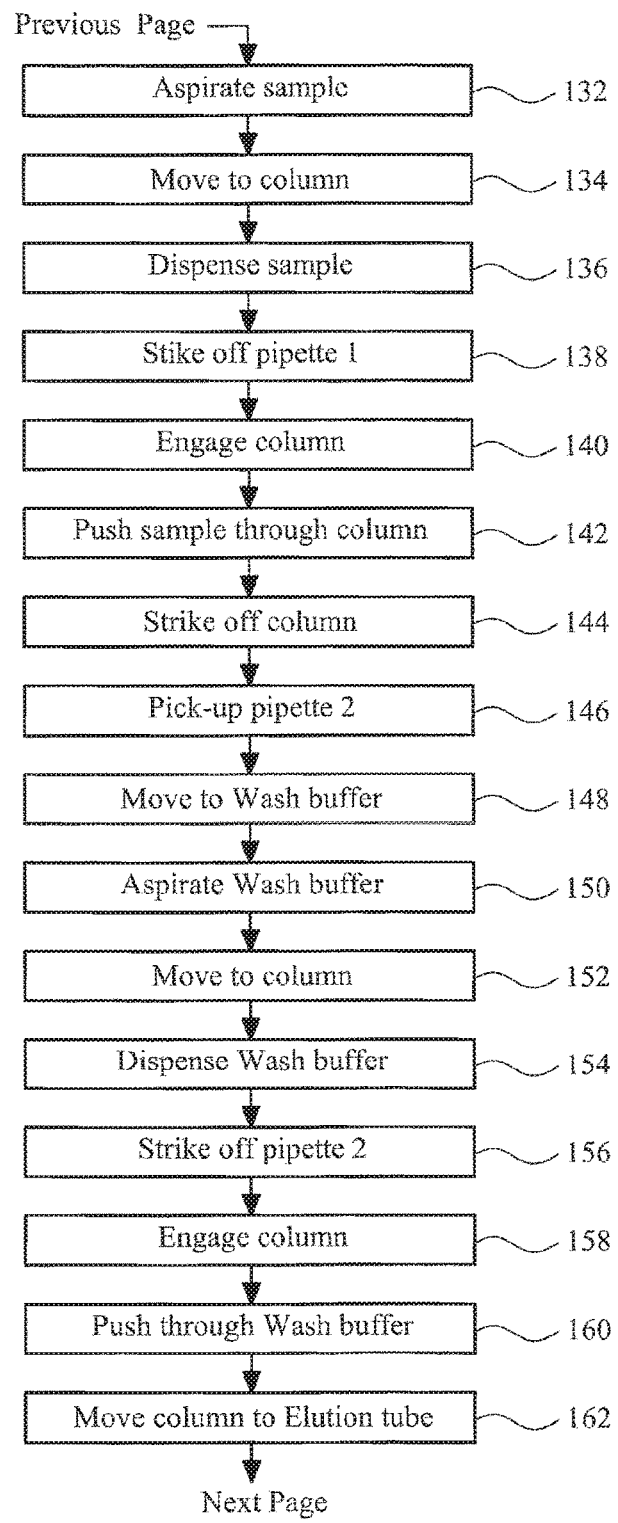
Figure 9C:
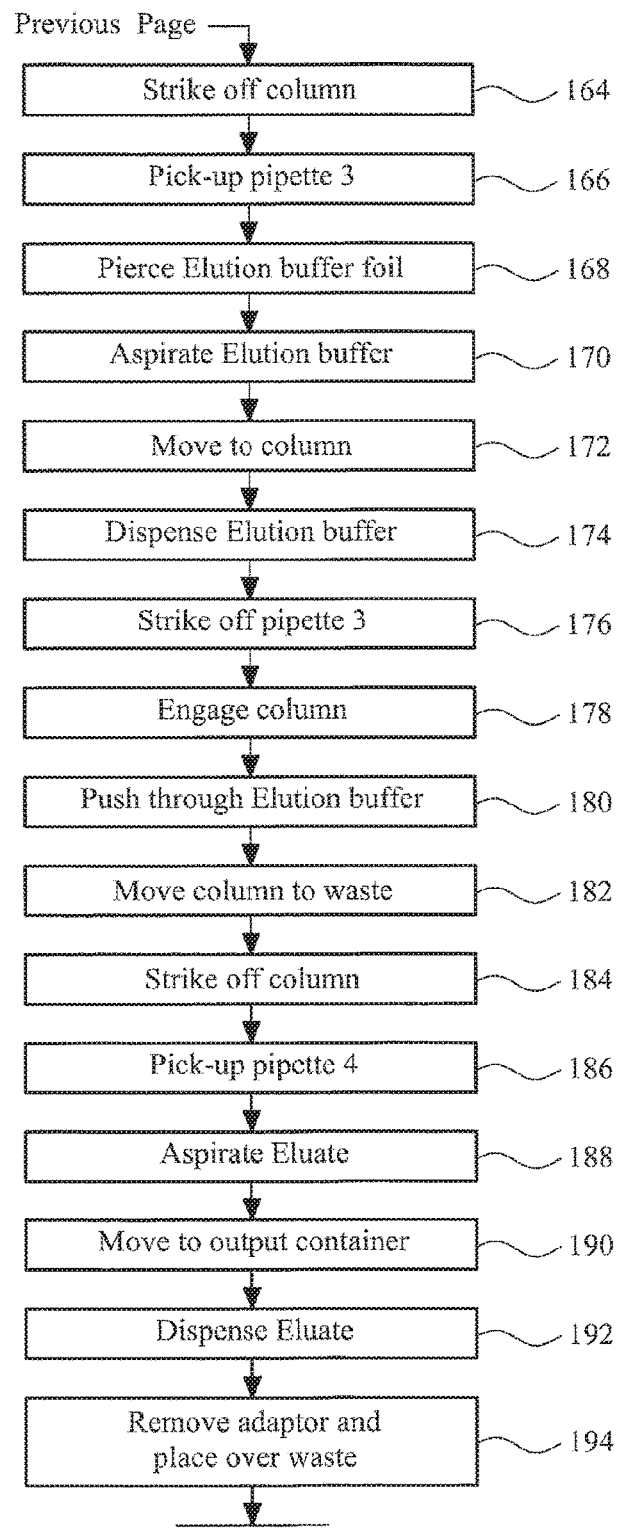
Figure 10A:
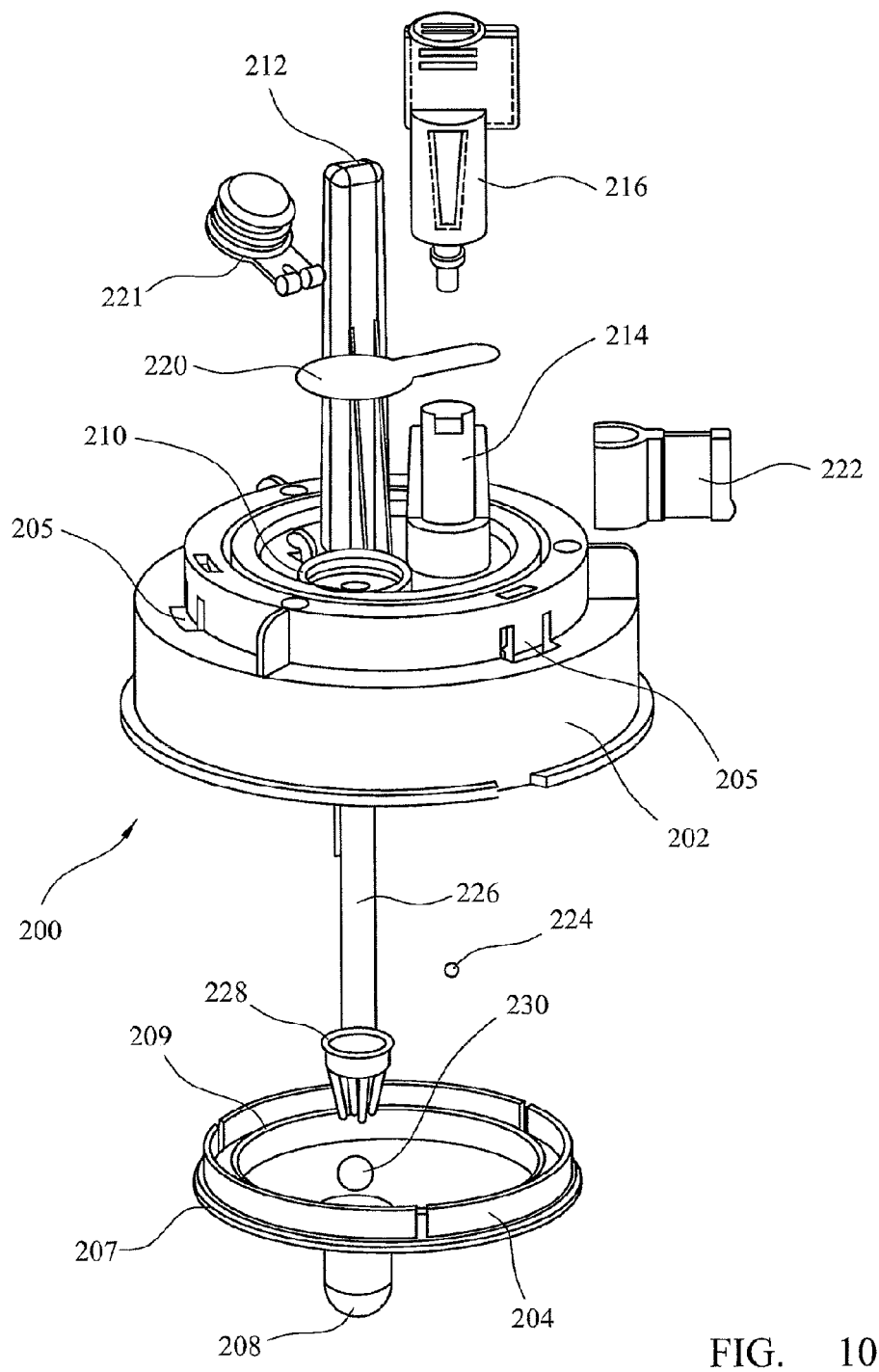
Figure 10B:
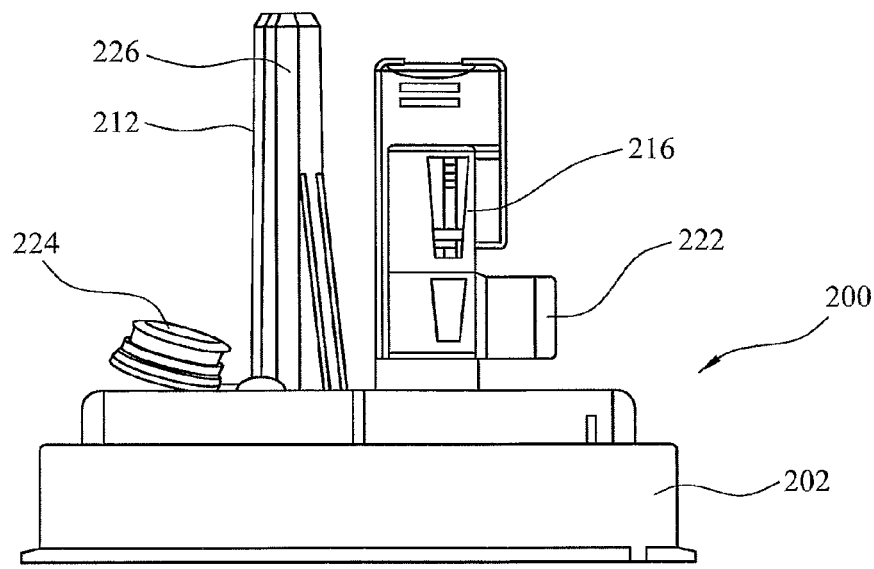
Figure 10C:
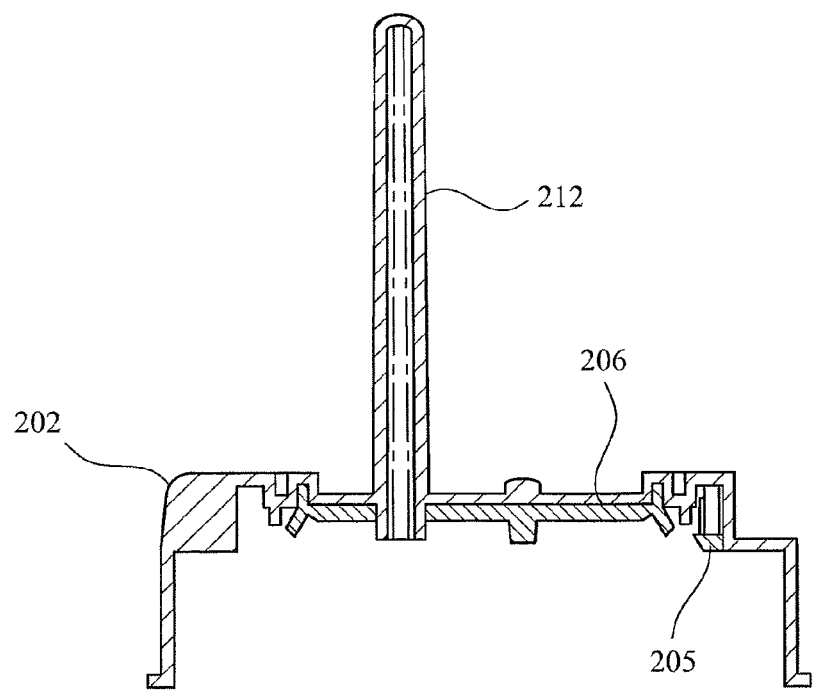
Figure 11:
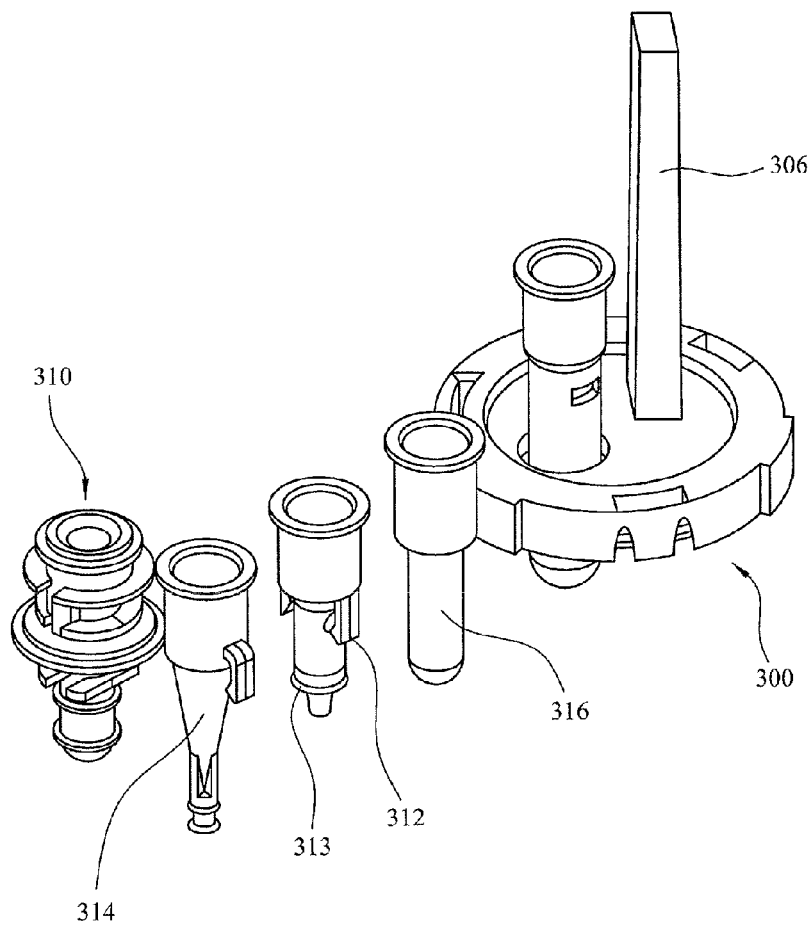
Figure 12:
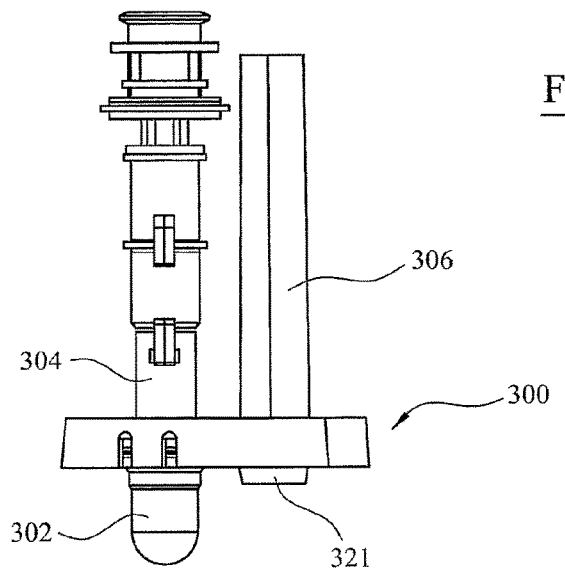
Figure 13:
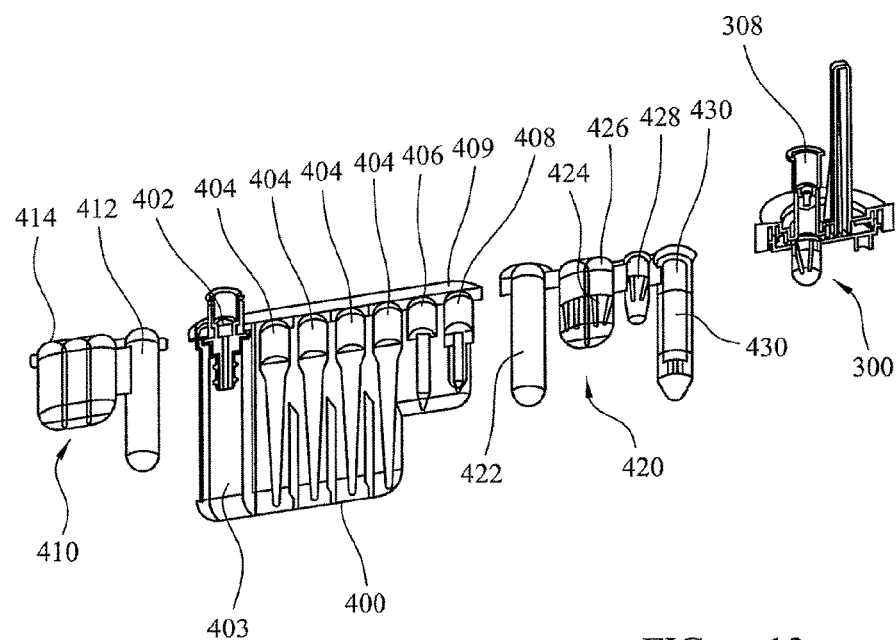
Figure 14A:
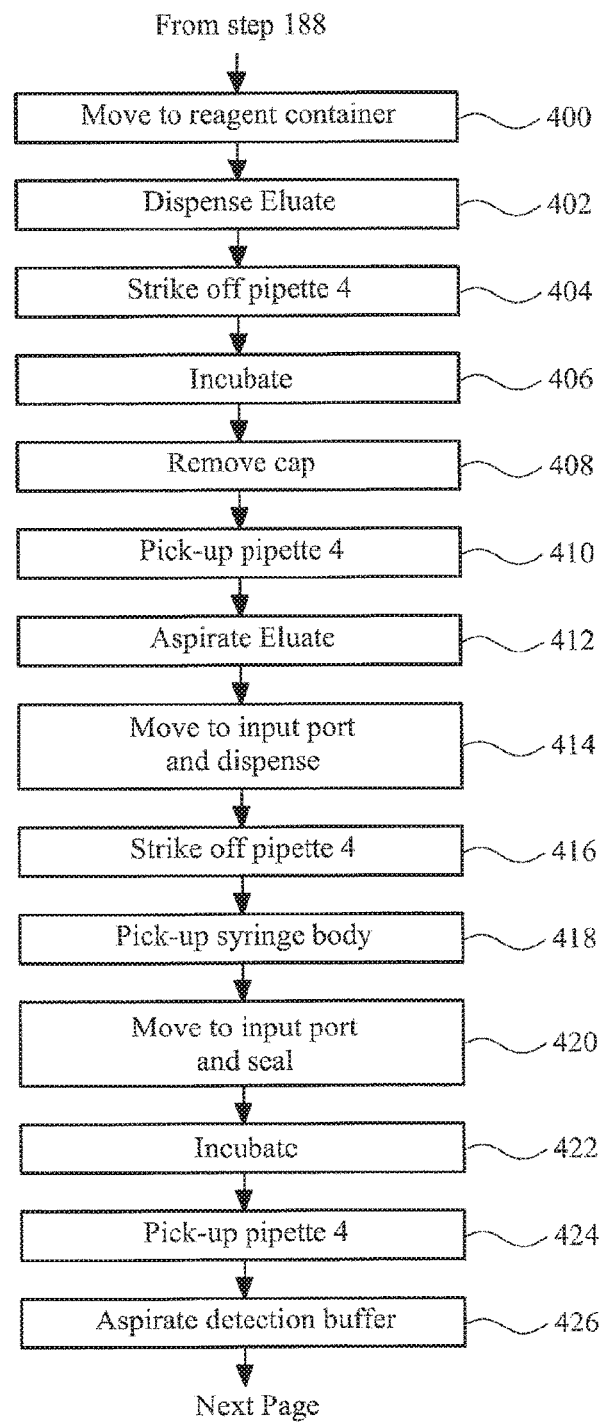
Figure 14B:
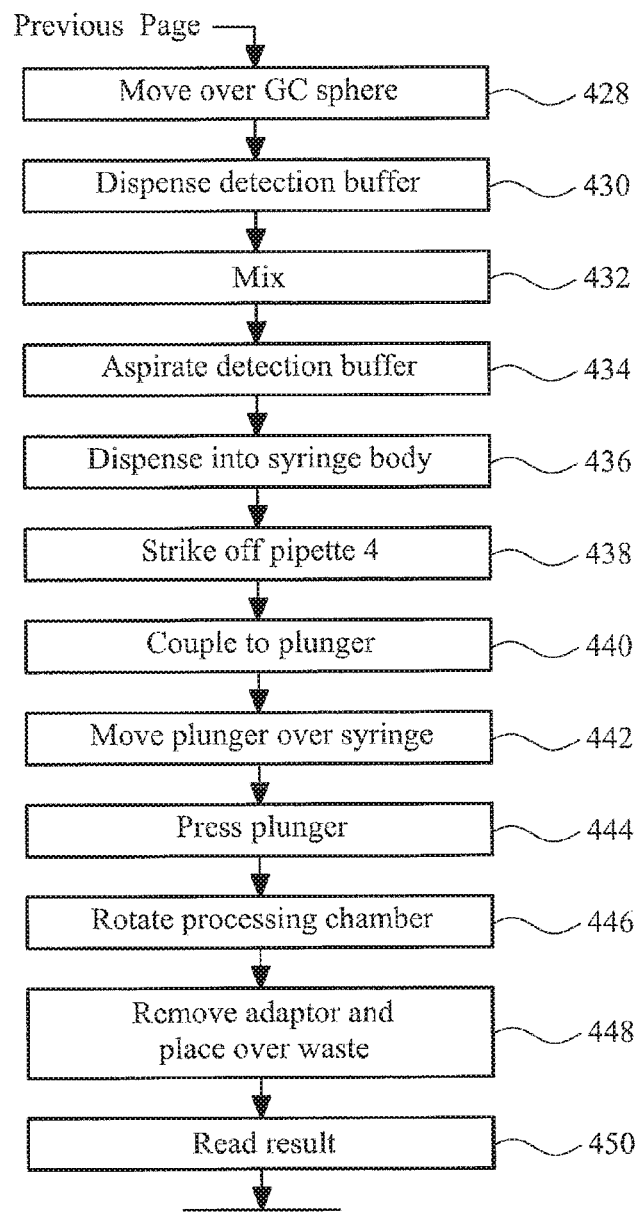
Figure 15:
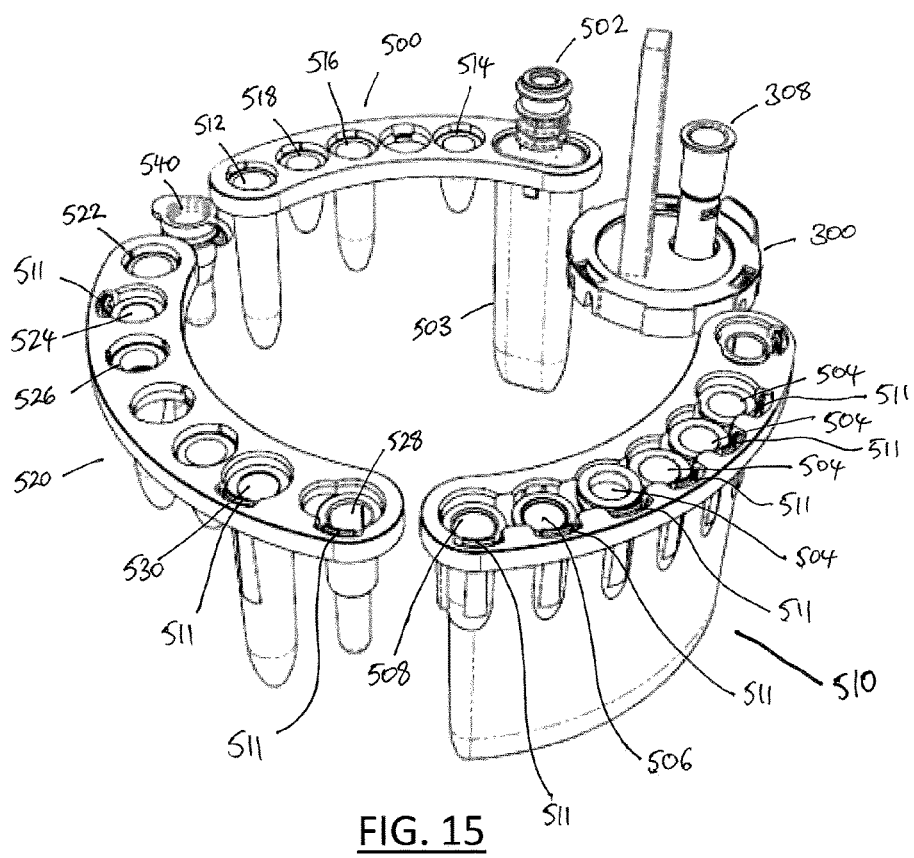
Figures 16A, 16B:
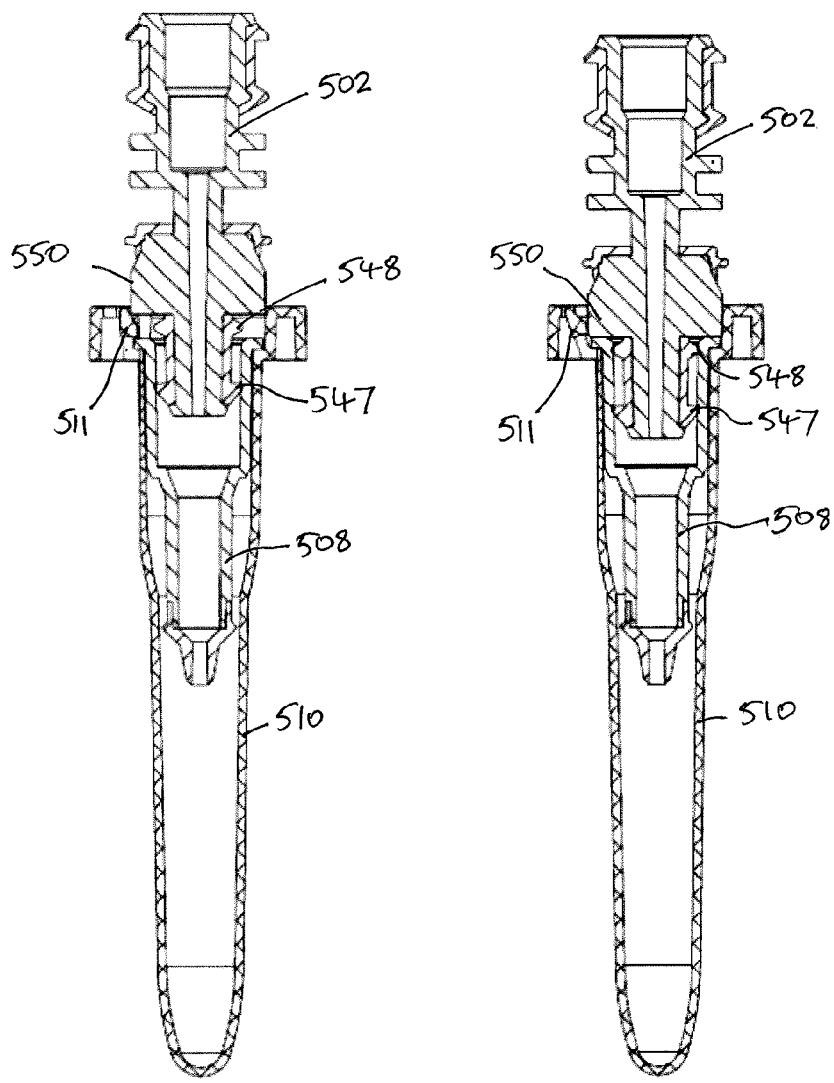

FIGS. 9A-9C collectively show a flow diagram illustrating the steps of a method in accordance with the invention;

FIG. 10a is an exploded view of a testing device for processing a sample obtained according to the method described with reference to FIGS. 9A-9C;

FIG. 10b is a side view of the testing device of FIG. 10a;

FIG. 10c is a cross section of the upper portion of the testing device shown in FIG. 10a;

FIG. 11 illustrates a testing kit that can be used in an automated process with an apparatus of the type shown in FIG. 1, prior to use;

FIG. 12 illustrates a portion of the testing kit of FIG. 11 during use;

FIG. 13 illustrates a complete sample processing and testing kit for use with an apparatus of the type shown in FIGS. 1 and 2, including an testing kit as described with reference to FIG. 11;

FIGS. 14A-14B collectively show a flow diagram illustrating the steps of an automated amplification stage of a method in accordance with the invention;

FIG. 15 illustrates an alternative complete sample processing and testing kit for use with a modified apparatus of the type shown in FIGS. 1 and 2;

FIG. 16a is a cross section through a cartridge shown in FIG. 15 prior to the adaptor fully engaging the syringe; and FIG. 16b is a cross section through a cartridge shown in FIG. 15 with the adaptor fully engaging the syringe.

As previously described the basic steps in a method to isolate nucleic acids from a sample of cells are (i) lysis of the sample to release nucleic acid from the cells, (ii) capturing nucleic acid by binding it to a solid phase, (iii) washing the captured nucleic acid to remove the remaining unwanted parts of the sample, and (iv) releasing the nucleic acid from the solid phase using an elution buffer. In addition to these basic steps, proteinase K can be added to the lysed sample to increase yield and reduce contamination.

This process requires pipetting, mixing and removal of various buffer solutions at different stages. FIG. 1 is a perspective view of an apparatus that is able to perform these steps in an automated fashion, and that can process several samples in parallel, but is still relatively compact and inexpensive.

The apparatus shown in FIG. 1 is configured to operate on four samples in parallel. The apparatus accordingly comprises four identical rows or tracks 10 of pipettes, reagents, columns and sample containers. These rows comprise several openings configured to receive various containers (as described with reference to FIG. 5 below) within a base containing at least two thermally controlled blocks. The four rows allow four samples to be processed in an identical manner in parallel. The apparatus may be designed to have any number of rows to allow any number of samples to be processed in parallel, as desired.

Above the base there is an air-piston apparatus 20 mounted on a transport apparatus 30. The air-piston apparatus 20 comprises four cylinders within the air-piston apparatus housing 21 and four pistons 22 movably received in the cylinders. The pistons 22 are mounted to a piston block 23. The piston block is fixed to a pump motor 36. The pump motor operates to drive the piston block up and down screw thread 38 to provide movement of the pistons relative to the cylinders. Screw thread 38 is fixed to the air-piston apparatus housing 21. Pump motor 36 in this example is a linear hybrid motor. The action of driving the piston block 23 causes air to be drawn into or ejected from the cylinders and can be accurately controlled to provide for movement of precise air volumes. Each cylinder has a socket, each socket configured for receiving an adaptor 40.

In FIGS. 1 and 2 the apparatus is shown with adaptors 40 engaged in the air-piston apparatus 20. Each adaptor 40 is also configured to engage with the pipettes and column, as described in detail below. The pump motor 36 is controlled by a suitable controller. The air-piston apparatus is thereby configured to controllably push and draw selectable volumes of air through each socket into order to move reagents into and out of the pipettes and columns.

The transport apparatus 30 is configured to allow the air-piston apparatus to be accurately and repeatedly moved both in the vertical direction and along the rows 10 in the base. The transport apparatus shown in FIGS. 1 and 2 supports the air piston apparatus in a cantilever arrangement from a movable column 32 above the tracks 10. However, other arrangements such as supporting the air piston apparatus on a movable gantry are also possible. The transport apparatus comprises a first stepper motor (not visible in FIGS. 1 and 2) beneath the horizontal track 34 formed in the base, configured to move transport column 32 along the track 34 and a second stepper motor (not visible in FIGS. 1 and 2) within the column 32 configured to move the air-piston apparatus 20 up and down relative to the transport column 32. The transport apparatus can be constructed in a number of different configurations, as would be appreciated by a person skilled in the art. In the example shown in FIG. 1 the stepper motors used in the transport apparatus 30 are rotational stepper motors.

Figure 3:
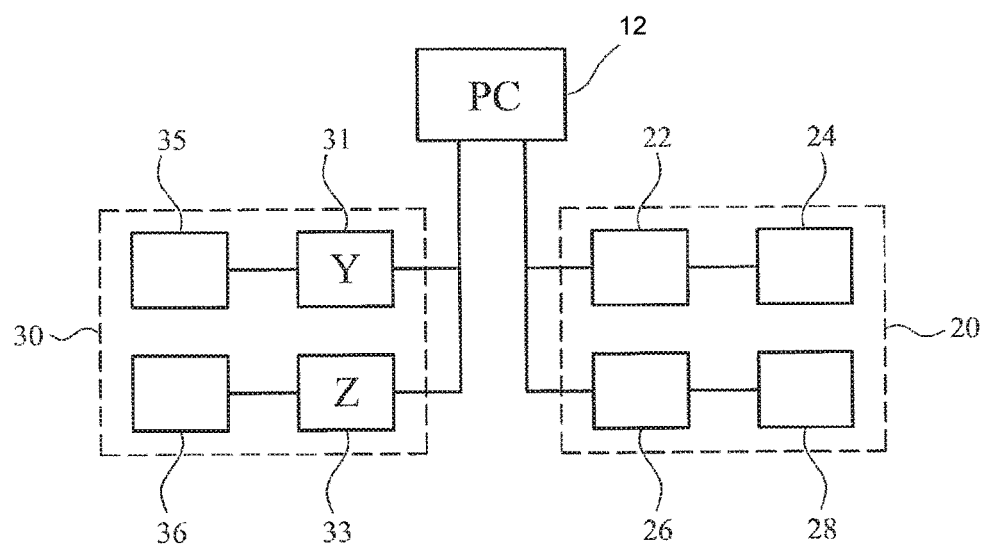
FIG. 3 is a schematic illustration of the control elements of the present invention.

The air-piston apparatus 20 and the transport apparatus 30 are automatically controlled during a sample processing sequence. As illustrated in FIG. 3, control circuitry for the transport apparatus 30 and for the air-piston apparatus 20 is connected to a PC 12. The control circuitry for the transport apparatus comprises separate Y and Z control circuits 31, 33 for the respective stepper motors 37, 39. The control circuitry 22 for the air-piston apparatus controls the pump motor 36 of the air-piston apparatus 20. Control circuitry 26 controls the movement of a striker plate motor 29 on the air-piston apparatus used to push the pipettes and columns out of engagement with the air-piston apparatus 20. The PC executes a program to instruct the control circuitry to operate the apparatus according to a desired sequence of processing steps in a processing protocol, an example of which is described with reference to FIGS. 9A-9C. Control of the thermal blocks is performed separately to the program executed by the PC. As an alternative to a PC, a microprocessor may be used to control the air piston apparatus and transport apparatus, as well as the thermal blocks. A display and user interface may be integrated into the apparatus so that no separate computing device is required.

The transport apparatus moves to each of the required locations on the track 10 to allow the air-piston apparatus to perform the required sample processing steps.

Figure 4:
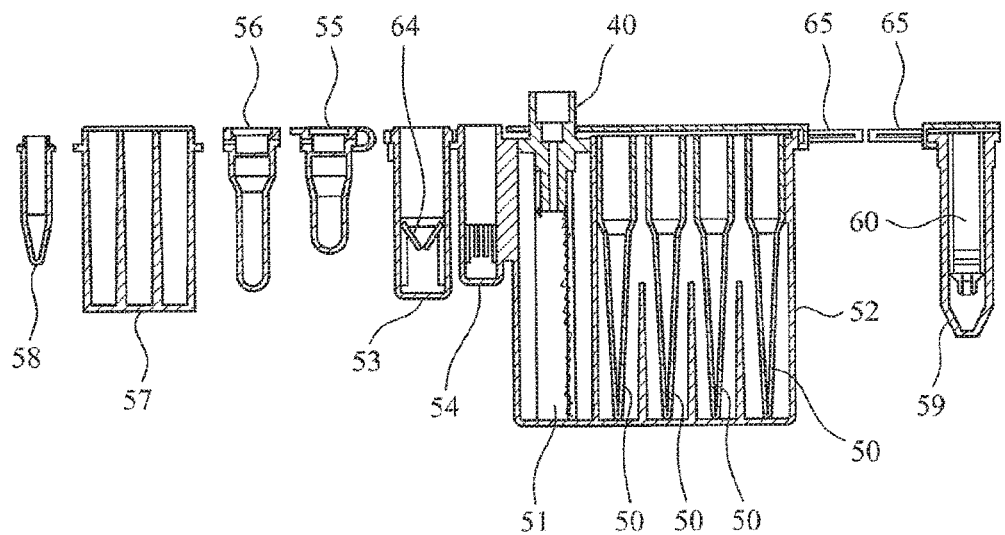
FIG. 4 illustrates a processing kit for use with an apparatus of the type shown in FIGS. 1 and 2.

FIG. 4 illustrates a kit of containers holding for reagents and samples for use in one of the tracks 10 of the apparatus shown in FIG. 1. The kit comprises a dry cartridge 52 containing four pipettes 50 and a waste container 51. An adaptor 40 is initially positioned in the waste container 51 and seals the waste container. The dry cartridge also includes containers for solid reagents. Container 53 contains a freeze dried ball of proteinase K and is sealed with a foil seal. Container 54 contains a freeze dried wash sphere and is sealed with a foil seal. The kit also comprises containers for blood samples. In the example shown in FIG. 4, there is a whole blood container 55 for containing a whole blood sample and a plasma container 56 for containing a plasma sample. These are provided as alternatives as the apparatus can process either type of sample. The kit further comprises a wet cartridge 57 for containing wet reagents, such as wash, lysis and elution buffer solutions and an output tube 58 for holding the processed sample at the end of processing. The kit further comprises an elution container 59 holding a column 60 containing a solid phase to which nucleic acid selectively binds.

It should be clear that different arrangements are possible for the kit of containers, with different reagents, different numbers of cartridges and different combinations of reagents, pipettes and columns in each cartridge. Reagents may be provided in wet form or in dry form together with a separate diluent depending on the stability of the reagent.

The cartridges protect the containers during transport and provide for easy handling before and after sample processing. The containers containing reagents are each provided with a pierceable seal, formed from laminated foil or plastic film. During operation of the apparatus, pipettes held in the air-piston apparatus are used to pierce the seals in order to access the contents of the containers, as described with reference to FIGS. 9A-9C. The waste container 51 is initially sealed by adaptor 40. The dry cartridge 52 and the elution container 59 each have a sliding lid 65. The lid 65 on the dry cartridge ensures that the adaptor is retained in position during transport. The sample containers are provided with integral sealing lids which are also piercable. The entire kit may be held within a sterile pouch or container prior to use.

In use, the appropriate containers are put into pre-assigned openings in the track. In this example, each track initially comprises a container containing a blood sample to processed, a container of lysis buffer, a container of solid proteinase K, four clean pipettes, the column containing a solid phase to which nucleic acid selectively binds, a container of elution buffer, and a container of wash buffer.

The initial positions are not critical as long as they are known and reflected in the sequence of movements specified in the program executed by the PC 12. However, as will be described, the samples are incubated at different temperatures during different stages of the sample processing protocol and so some containers are placed in one thermally controlled block and other in another thermally controlled block as required.

The apparatus may include a locking cover plate that covers the tracks ain a locked position and comprises a plurality of openings corresponding to the openings in each track but sized to retain the cartridges in place while allowing the pipettes and column to be moved and allowing the pipettes to access the various reagent containers. The locking cover plate may be configured to close a switch when in a locking position such that transport apparatus and air-piston apparatus cannot be operated until the locking cover plate is in a locking position.

Figure 5B:
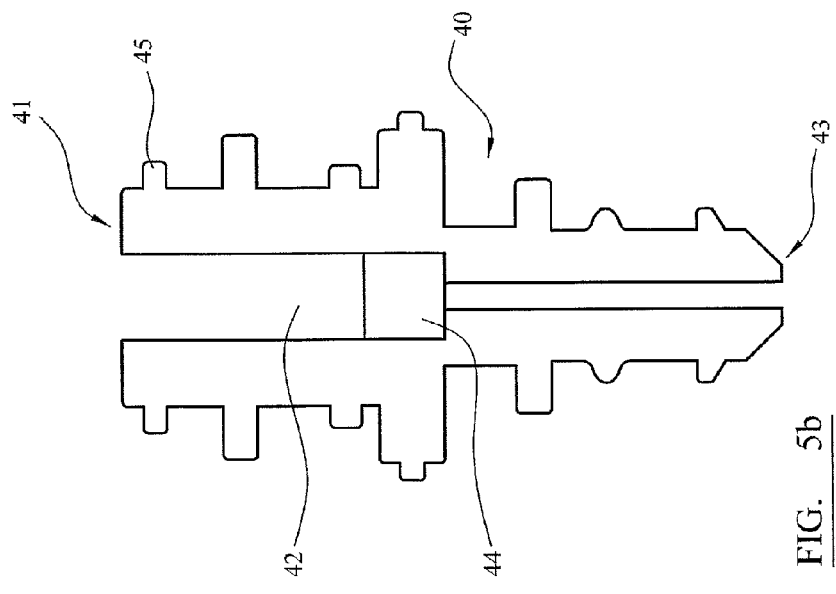
Figure 5A:
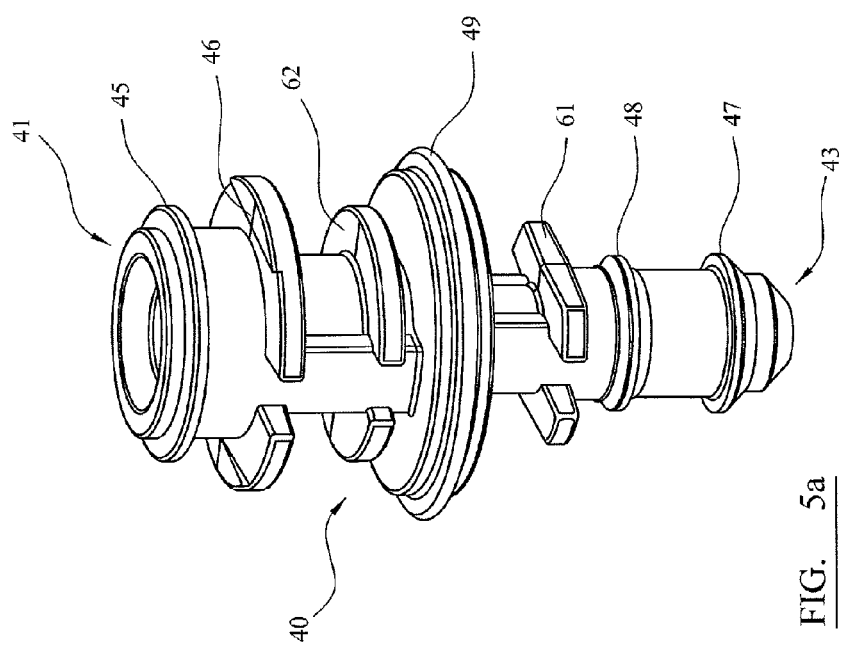
FIG. 5a is a perspective view of an adaptor for use with the apparatus shown in FIG. 1.
Figure 6:
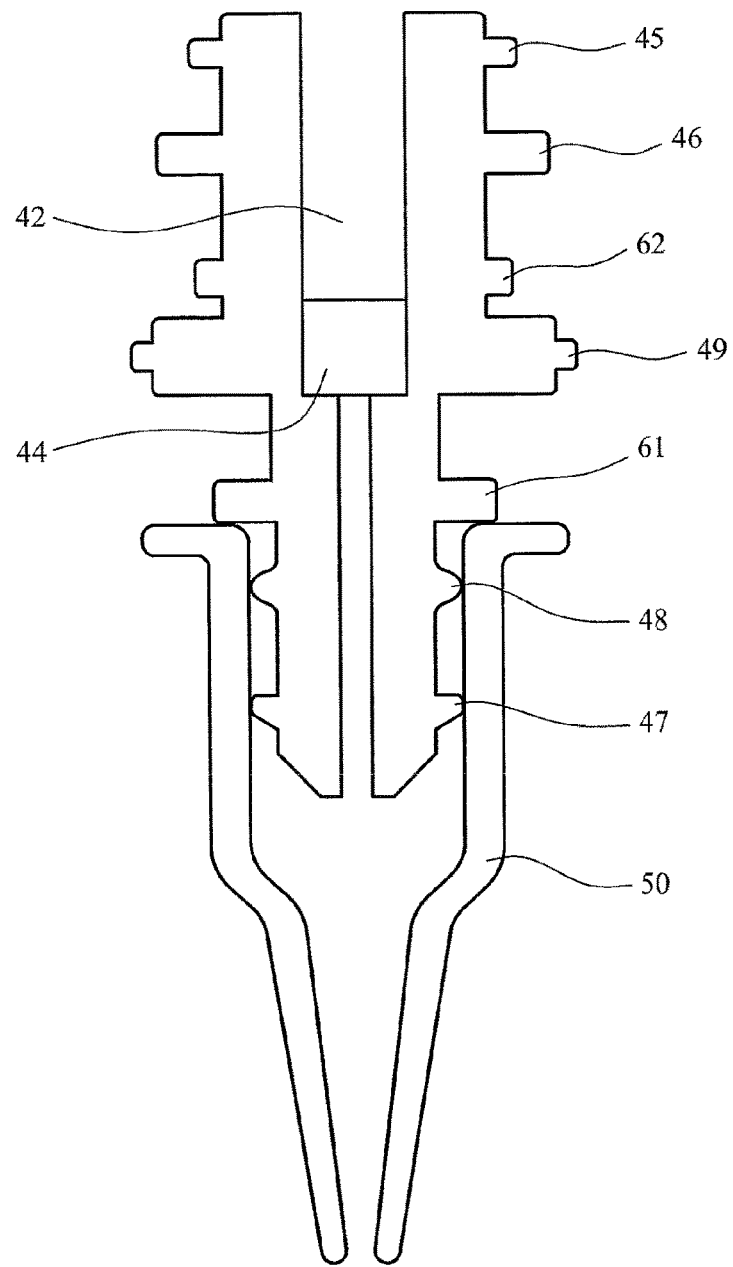
FIG. 6 is a cross section view of the adaptor of FIG. 4 engaged with a pipette.

The adaptors 40 are used to couple the air-piston apparatus 20 to various components in each row, as is described with reference to FIGS. 9A-9C. Each adaptor is a disposable item that may be formed from moulded plastics materials. An adaptor 40 is shown in FIGS. 5, 5a and 6. FIG. 5a is a perspective view of adaptor 40. FIG. 5b is a cross-section of the adaptor of FIG. 5a.

The adaptor 40 has an essentially cylindrical shape with a bore 42 extending from a first end 41 for engagement with the air-piston apparatus and a second end 43 for engagement with pipettes and the column. The bore 41 allows the air-piston apparatus 20 to push air into and draw air out of a pipette or column. A filter 44 is provided within the bore to prevent liquids, and in particular aerosol droplets, from passing into the air-piston apparatus. The filter in this embodiment comprises sintered polyethylene and has an average pore size of 7 μm. Suitable filter materials include the WON 3.2M material from Porvair Technology, Clywedor Road South, Wrexham Ind Est, Wrexham, UK and the CS-1142 filter material from Porex Technologies GmbH, Produktion and Produktentwicklung, Industriestraße 02692 Obergurig OT Singwitz, Germany.

An upper sealing ring 45 is provided to seal against a socket in the air-piston apparatus. It is advantageous to provide the sealing ring on each adaptor rather than within each socket of the air-piston apparatus as the adaptors are disposable items. The sealing rings inevitably wear during use and would be difficult to maintain within the permanent sockets of the air-piston apparatus. An adaptor lock 68, shown in FIGS. 1 and 2, consisting of a sliding plate with slots cut into it, each slot corresponding to a socket on the air piston apparatus, engages with upper lugs 46 on the adaptor to ensure the adaptor 40 is retained in the socket. The upper lugs 46 also prevent the adaptor from travelling too far into the socket.

A pair of axially spaced lower sealing rings 47, 48 is provided on the lower end of the adaptor 40 to seal against an inner surface of the pipettes 50 and an inner surface of the column 60. The pair of lower sealing rings 47, 48 not only provide an air tight seal but also ensure that the pipette (or column) coupled to the adaptor is correctly oriented and not tilting, so that its dispensing end is in a predictable and desired position. FIG. 6 shows the adaptor 40 engaged with a pipette 50. The pipette has an upper portion with a cylindrical inner surface that engages the lower sealing rings 47, 48 on the adaptor. The cylindrical inner surface extends over a greater axial length than the axial spacing between the two lower sealing rings 47, 48.

A circular closure seal 49 is also provided on the adaptor. The closure seal 49 extends laterally beyond the lower sealing rings 47, 48 and is shaped to provide a sealing lid for a correspondingly shaped container, such as a container for waste products produced during the sample processing protocol.

A pair of lower lugs 61 is provided above the lower sealing rings 47, 48. The lower lugs 49 prevent a pipette or column from riding too high on the adaptor 40, as shown in FIG. 6. A pair of positioning lugs 62 is provided between the closure seal 49 and the upper lugs 46. The positioning lugs 62 allow a striker plate on the air-piston apparatus 20, or an adaptor comb 90, to engage and disengage the adaptor 40 from the air-piston apparatus 20, as is described with reference to FIGS. 9A-9C.

Figure 7A:
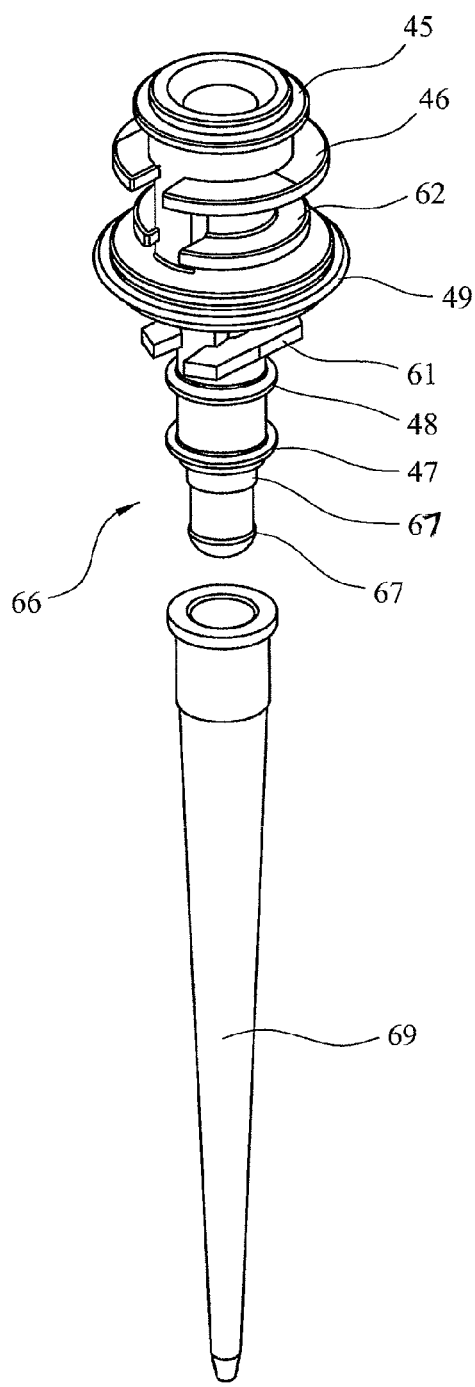
FIG. 7a is a perspective view of an alternative adaptor for use with the apparatus shown in FIG. 1 together with a pipette.
Figure 7B:
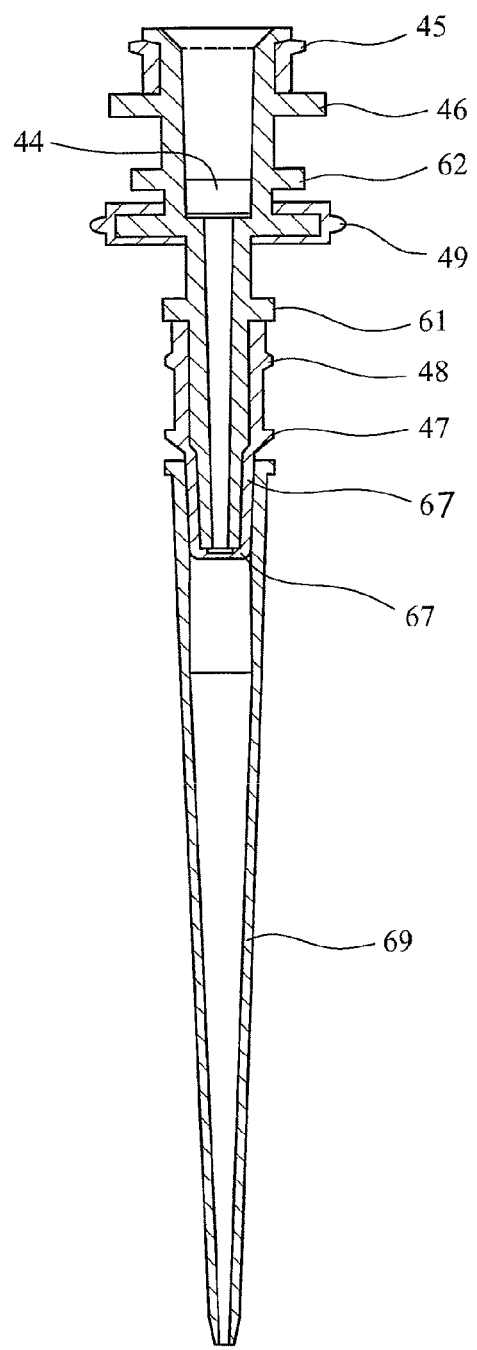
FIG. 7b is a cross section view of the adaptor of FIG. 7a engaged with the pipette.

It may desirable to allow the adaptor to engage pipettes, containers and columns of different diameter. For example, to reduce the overall size of the apparatus it may be advantageous to provide pipettes with a small diameter than the column. FIGS. 7a and 7b show an alternative adaptor design configured to engage different diameter components. The adaptor of FIGS. 7a and 7b is essentially the same as the adaptor described with reference to FIGS. 5a, 5b and 6 but with the addition of an additional narrower section 66 on the second end, incorporating additional lower sealing rings 67 configured to provide a seal with a smaller pipette 69. FIG. 7b shows the adaptor engaged with the smaller pipette 69. It can be seen that the pipette 69 cannot ride higher that seal 47 on the adaptor but that sealing rings 67 provide seals and ensure correct alignment of the pipette on the adaptor. An adaptor aw shown in FIGS. 7a and 7b allows the adaptor to sealingly engage two different sizes of component. Clearly, an adaptor with a series of stepped pairs of sealing rings may be provided to allow a series of differently sized components to be engaged.

The striker plate 28 is shown in FIG. 2 and is fixed to the air-piston apparatus 20. The striker plate is movable by a servo motor 29 up and down relative to the sockets on the air-piston apparatus. The striker plate comprises four, open-ended slots that align with the sockets in the air-piston apparatus into which the adaptors 40 can fit. The slots are dimensioned to fit around the adaptors between the upper lugs 46 and the positioning lugs 62. However, the upper end of any pipette or column engaged with the adaptor cannot pass through the slots of the striker plate 28, so that downward movement of the striker plate relative to the adaptor can be used to push the pipette 50 or column 60 off the adaptor 40.

The apparatus also includes an adaptor comb 90, which is a plate having four slots 92 formed in it, positioned above the base at one end of the base. The four slots 92 are spaced to match the spacing of the sockets in the air-piston apparatus 20. The adaptor comb is used to disengage the adaptor from the air-piston apparatus after sample processing has been completed, as is described with reference to FIGS. 9A-9C.

As an alternative to the use of adaptor comb 90 and a sliding adaptor lock 68, a second striker plate may be fixed to the air piston apparatus. The first striker plate may be used for engaging and disengaging the pipettes and column (and any other components) from the adaptor. The second striker plates may be used for engaging and disengaging the adaptor with the air-piston apparatus. The first and second striker plates may be driven by separate motors, each controlled by the PC or microprocessor.

Figure 8A:
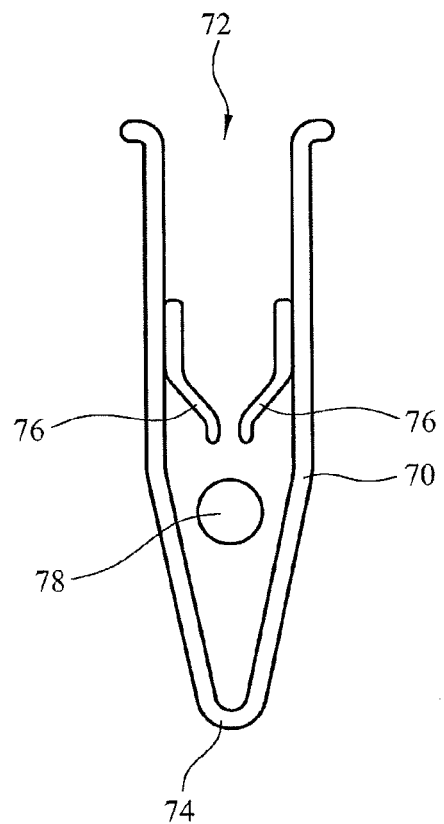
FIG. 8a is a side view of a container for a solid reagent in accordance with an aspect of the invention.
Figure 8B:
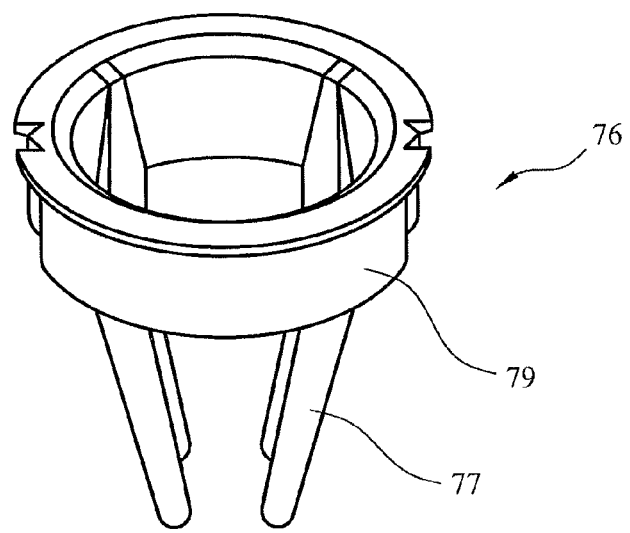

The containers 53 and 54 initially contain a solid reagent in the form of a ball or pellet. For example proteinase K may be provided in a freeze dried ball. An exemplary container 70 for a freeze dried reagent 78 is shown in FIG. 8a. The container 70 comprises a conventional outer body and has an open end 72 through which solid reagent 78 is loaded into the container and through which lyophilised reagent may be removed. The container includes an insert 76, shown in isolation in FIG. 8b, comprising an upper ring 79 and a plurality of flexible but resilient protrusions 77 or fingers extending from the side wall towards the closed end 74 of the container and extending inwardly. The insert 76 has a plurality of circumferentially spaced protrusions 77. The ends of the protrusions 77 are spaced from one another by a distance smaller than the minimum lateral dimension of the solid reagent 78. Some of the protrusions may be flared at their free ends or may be joined to one another. When the solid reagent is loaded into the container the flexible protrusions 77 flex to allow the reagent to pass the protrusions and locate in the closed end 74 of the container. The protrusions 77 then return to their original position. The solid reagent cannot then re-pass the protrusions to leave the container through the open end. It is only when reconstituted in liquid form that the reagent can leave the container. The insert 76 can be simply pushed into the container 70 and retained by a friction fit or by engaging moulded recesses in the container 70.

FIGS. 9A-9C collectively show a flow chart illustrating one sequence of steps performed by the apparatus described with reference to FIGS. 1 to 8b, to carry out a processing protocol.

In a first automated step, step 100, the transport apparatus moves the air-piston apparatus to pick-up and engage the adaptors 40. This step comprises moving the air-piston apparatus to the initial position of adaptors and picking up the adaptors using the striker plate 28. The striker plate engages under the upper lugs 46 or positioning lugs 62. The striker plate is then lifted to push the adaptors 40 into the sockets. The transport apparatus may additionally press the lower end of the adaptors against a side wall of one of the cartridges to push the adaptors into the sockets more securely. The sliding adaptor lock 68 is used to secure the adaptors after they are inserted into the sockets.

In step 102 the transport apparatus 30 moves to engage the adaptors 40 with the columns of solid phase material 60. The adaptors 40 are simply moved into position directly above the columns 60 before moving down to engage the adaptors with the open ends of the columns 60.

In step 104 the columns 60 are moved by the transport apparatus to the waste container 51. In step 106 the striker plate 28 is positioned below the closure seals 49 and moved down to push the columns 60 off the adaptors 40.

In step 108, a first set of pipettes 50 are engaged with the adaptors 40. Again, the transport apparatus simply moves the adaptors to a position directly above the pipettes 50 and then moves down to engage the pipettes, as shown in FIG. 6.

In step 110 the first pipettes are moved to pierce the foil seals on the containers 53 holding the proteinase K. The dispensing ends of the pipettes are tapered and sufficiently narrow to pierce the foil seals when moved down by the transport apparatus. In step 112 the foil seals on the containers 57 holding the lysis buffer are pierced in the same manner.

In step 114, the pipettes having pierced the foil seals are lowered so that their dispensing ends are within the lysis buffer, and a predetermined volume of lysis buffer is aspirated, i.e. drawn into the pipettes, by the air-piston apparatus 20. In step 116, the pipettes are moved back to the container 53 housing the proteinase K. In step 118 the lysis buffer is dispensed from the pipettes into the proteinase K containers 53 by the air-piston apparatus 20. In step 120 the proteinase K and lysis buffer is mixed by repeatedly aspirating and dispensing the mixture into the container 53 using the pipettes.

In step 122 the pipettes are moved to pierce the cap of the sample containers 55. In step 124 the samples are aspirated in to the pipettes 50. The pipettes are then moved back to the proteinase K containers 53 in step 126 and the samples dispensed into the lysis buffer, proteinase K mixtures in step 128.

In step 130 the samples, lysis buffer and proteinase k are mixed by repeated aspiration and dispensing and incubated in the thermal block at between 19 and 21° C. for a predetermined time, typically around 15 minutes, until the lysing process is complete.

In step 132, the lysed samples are aspirated into the pipettes 50. In step 134 the samples are moved above the columns 60 in the waste containers 51. In step 136 the lysed samples are dispensed into the columns 60.

In step 138 the first pipettes 50 are moved back to their initial positions and are pushed off the adaptors by the striker plate 28. In step 140 the adaptors are then moved back to engage with the columns 60. In step 142, the air-piston apparatus 20 dispenses a controlled volume of air into the columns 60 to push the samples through the columns. In this embodiment, the volume of air between the air piston apparatus and the top of the column is substantially halved. In this process the nucleic acid in the lysed samples binds to the solid phase in the columns. When dispensing the controlled volume of air, the air-piston apparatus applies a pressure above atmospheric pressure to the column. The higher the pressure applied, the faster the samples are pushed through the column. However, it has been found that if too high a pressure is applied to the column the yield of nucleic acid is reduced. It has been found that peak applied pressures of at least 0.2 bar but below 2 bar above atmospheric pressure provide good results. The pressure may be applied continuously or variably, such as in a stepwise fashion. More preferably the peak applied pressure is between 0.4 bar and 1.5 bar above atmospheric pressure. In this particular embodiment a peak applied pressure of between 0.7 and 1 bar above atmospheric pressure has been found to be optimal. However, the skilled person may optimise the applied pressure and volume of air according to the dimensions of the system and the nature of the samples being processed.

In step 144 the striker plate 28 pushes the columns 60 out of engagement with the adaptors.

In step 146 the transport apparatus moves the adaptors to engage a second set of pipettes 50. These pipettes are then moved to pierce the foil sealing the containers 57 of wash buffer in step 148. In step 150 the wash buffer is aspirated into the pipettes 50. In step 152 the pipettes of wash buffer are moved to a position above the columns 60. The wash buffer is then dispensed in to the columns in step 154.

In step 156 the second pipettes are moved back to their initial positions and are pushed off the adaptors 40 by the striker plate 28. In step 158 the adaptors 40 are again moved to engage the columns 60. In step 160 the air-piston apparatus 20 dispenses a controlled volume of air into the columns to push the wash buffer through the columns.

In step 162 the columns, still engaged with the adaptors 40, are moved to the elution tube 59 at a different position along the row 10. The elution tube is positioned in a different thermal block and held at between 76 and 80° C. In step 164 the striker plate 28 disengages the columns from the adaptors 40.

In step 166 the transport apparatus moves the adaptors 40 to engage the third set of pipettes 50. These pipettes 50 are then moved to pierce the foil sealing the containers 57 of elution buffer in step 168. In step 170 the elution buffer is aspirated into the pipettes. In step 172 the pipettes of elution buffer are moved to a position above the columns 60. The elution buffer is then dispensed in to the columns in step 174.

In step 176 the third pipettes are moved back to their initial positions and are pushed off the adaptors 40 by the striker plate 28. In step 178 the adaptors 40 are again moved to engage the columns 60. In step 180 the air-piston apparatus 20 dispenses a controlled volume of air into the columns 60 to push the elution buffer through the columns 60.

In step 182 the columns 40, still engaged with the adaptors 40, are moved back to the waste container 51. In step 184 the columns are pushed off the adaptors 40 by the striker plate 28.

In step 186 the transport apparatus moves the adaptors to engage a fourth set of pipettes. These pipettes are then moved in step 188 to the elution tube 59 and the eluate, i.e. the eluted nucleic acid, is aspirated into the fourth pipettes. The fourth pipettes are then moved above the output containers 58 in step 190 and dispensed into the output containers in step 192. The sample processing is then complete.

In step 194 the used containers may be moved back into desired positions for disposal or recycling by the operation of the transport apparatus 30 and the striker plate 28 in the same manner as already described. For example, the columns 60 may be moved back to the elution tubes. The adaptors may be disengaged from the air-piston apparatus 20 and placed on the waste container 51 to seal the waste container for subsequent transport and disposal.

The disengagement of the adaptors from the air-piston apparatus may be carried out by moving the adaptors into the adaptor comb 90 and pulling the air-piston apparatus up. The positioning lugs 62 retain the adaptors in the comb 90, disengaging the adaptors from the air-piston apparatus. The adaptors may subsequently be picked up by the striker plate engaging the upper lugs 46 and then moved to the waste containers 51 by the transport apparatus. The striker plate is finally disengaged from the adaptors and then used to push the adaptors 50 down to seal the waste containers.

Clearly the process described above is just one example of a sample processing protocol that can be carried using an apparatus and adaptors in accordance with the invention. Many different processing protocols are possible using different combinations of the same basic operations.

Following processing a sample in this way, the sample may be tested for the presence of a particular nucleic acid indicative of a particular pathogen or medical condition. This testing process consists of amplifying any of the nucleic acid present in the processed sample and then testing for the presence of the nucleic acid. The amplification and testing process may be carried out manually or automatically. However, it is crucial that the sample is protected from amplicon contamination during the amplification and testing process to prevent false results.

In a first example, the amplification and testing is carried out manually using a dedicated testing device 200 as shown in FIGS. 10a, 10b and 10c. FIG. 10b is an exploded view of the device 200 and shows the various components. FIG. 10b shows the device in an assembled condition.

The testing device 200 comprises an upper portion 202 and a lower portion 204 which are both formed from a mouldable plastics material. The upper and lower portions are both circular and rotatably engageable with each other. Lower portion 204 is retained by three circumferentially spaced clips 205 formed in the upper portion. FIG. 10c is a cross section of the upper portion 202 alone and shows one of the clips 205. The upper portion 202 has a downwardly extending circumferential lip whose lower edge acts as a stand for the device, as can be seen in FIG. 10b.

The upper portion 202 comprises an input opening 210, an analysis chamber 212 and a reagent input port 214. The lower portion 204 comprises a processing chamber 208. Between the upper portion and the lower portion is a resilient sealing element 206, shown in FIG. 10c. The resilient sealing element 206 is co-moulded with the upper portion 202. When the lower portion is engaged by the clips 205 of the upper portion 202, the lower portion 204 presses against the sealing element around a perimeter of the sealing element 206, thereby sealing the space interior of the perimeter of the sealing element 206 from the external environment.

The engagement of the lower portion 204 with the clips 205 allows the lower portion to rotate relative to the upper portion 202 so that the processing chamber 208 can be brought, sequentially, into an overlapping relationship with the input opening 210, reagent input port 214 and analysis chamber 212.

The processing chamber has an upwardly facing opening through which a sample and reagents can enter the processing chamber. The processing chamber contains a retaining element 228, of the type described with reference to FIG. 8b, for retaining a solid reagent 230 within the processing chamber. The retaining element 228 as shown has four retaining protrusions, but other configurations are possible. In one embodiment the retaining element comprises just two protrusions that flare outwardly at their free ends to provide a large engagement area with the solid reagent to prevent the solid reagent from escaping. The solid reagent 230 is preloaded into the processing chamber. In other words the device 200 is packaged with a solid reagent in the processing chamber prior to use.

The processing chamber is initially aligned with the input opening 210. The input opening 210 is initially sealed by a sealing foil 220. The sealing element 206 has an aperture corresponding to the input opening 210, as well as apertures corresponding to the reagent input port and the analysis chamber. A hinged closure 221 is provided for closing and sealing the input opening following the introduction of a sample into the processing chamber, as will be described.

The reagent input port 214 comprises a cylindrical chamber integrally formed in the upper portion 202. A plunger 216 is received through an open upper end of the reagent input port. A compliant gasket on a lower end of the plunger provides a seal with the inner wall of the reagent input port 214 in the manner of a syringe. An outer portion of the plunger is configured to pass around the outside of the reagent input port. An open lower end of the reagent input port is sealed in part by the sealing element 206. A reagent aperture in the sealing element 206 directly below the reagent input port is sealed by a glass bead 224. The reagent aperture in the sealing element is at the base of a funnel shaped portion of the sealing element. The glass bead 224 is held in the funnel shaped portion but, because of the compliant nature of the sealing element 206, is able to pass through the reagent aperture if sufficient pressure is applied to the bead 224. A reagent, in this example a detection buffer, is held within the reagent input port between the plunger and the glass bead.

A plunger retaining collar 222 is provided around the reagent input port 214. The engagement of the plunger retaining collar 222 with the outer portion of the plunger prevents the plunger being moved downwardly through the reagent input port to dispense the reagent and glass bead.

The analysis chamber 212 is a tall, thin chamber containing a test strip 226. The test strip 226 is held in the analysis chamber 212 by the lower portion 204 until the processing chamber is overlapping with the analysis chamber. The test strip can then drop into the processing chamber under the force of gravity. The analysis chamber is transparent to allow the test strip to be visually inspected. The device shown in FIGS. 10a and 10b is designed for on-site nucleic acid testing. The test strip 226 is accordingly sensitive to the presence of a particular nucleic acid and provides a visual indication, such as a colour change if it contacts a sample containing that nucleic acid.

The device shown in FIGS. 10a and 10b may be used in the following method. The sealing foil 220 is first removed. A blood sample, which may first have been processed by a system described with reference to FIGS. 1 and 2, is then introduced into the processing chamber and mixes with the solid reagent 230. The hinged closure 221 is then used to seal the input opening 210. The processing chamber is then incubated, typically by placing the device in a heat block having a receptacle shaped to receive the processing chamber.

When the incubation process has completed, the upper portion 202 is rotated relative to the lower portion until the processing chamber 208 is in an overlapping relationship with the reagent input port 214. The collar 22 is then removed and the plunger depressed until the outer portion of the plunger 216 contacts the upper portion 202. This applies sufficient pressure on the detection buffer and bead 224 within the reagent input port 214 that the sealing element deforms and allows the bead and detection buffer to enter the processing chamber.

The upper portion 202 is then further rotated relative to the lower portion to a final position in which the analysis chamber 212 is aligned with the processing chamber 208. The test strip 226 then drops into the processing chamber 208 so that its end is in contact with the processed sample. The processed sample is then wicked up the test strip 226 and the results of the test are obtained by visually inspecting the test strip.

The amplification and testing device shown in FIGS. 10a and 10b is sealed from the external environment immediately after the introduction of the sample into the processing chamber, and throughout amplification and detection. The device provides a closed system and the sample cannot escape from the device. The closed system helps eliminate contamination from external sources, which may produce false results, and at the same time protects the external environment from contamination with the amplified product of the processed sample. This is particularly important where processing of the sample involves the amplification of nucleic acid, as a small quantity of rogue nucleic acid could easily be amplified to provide a false result.

During processing, and in particular during inspection of the test strip, the amplification and testing device may be held in a warm environment in order to prevent condensation on the inside of the device which might make reading the result difficult. Alternatively, or in addition, the inside surface of the analysis chamber may be treated, by plasma treatment for example, to prevent or reduce droplets condensing onto the surface during processing.

In an alternative embodiment, the amplification and detection process may be carried out by a system of the type described with reference to FIGS. 1 and 2, as part of a processing protocol. In order to allow for this, the amplification and testing device of FIGS. 10a and 10b must be modified.

FIG. 11 is a perspective view of an amplification and testing kit for use in an automated process. The kit shown in FIG. 11 still has the advantage of providing a closed system during amplification and testing. The kit comprises a testing device 300 having an upper portion and a lower portion in the same manner as the device described with reference to FIGS. 10a and 10b. A processing chamber 302 is formed in the lower portion and contains a solid amplification reagent. An input port 304 and an analysis chamber 306 are formed in the upper portion. There is no separate reagent input port. A compliant sealing element, not visible in FIG. 11, is co-moulded with the upper portion, on the underside of the upper portion in the same manner as shown in FIG. 10c.

In an initial position the processing chamber 302 is aligned with the input port 304.

The input port 304 is sealed by a cap 308. The cap has a sealing portion 326, which includes a compliant gasket, and an adaptor coupling portion 328. The adaptor coupling portion 328 is cup shaped with an open end configured to receive an adaptor 310 of the type described with reference to FIGS. 5a and 5b. The adaptor coupling portion has an inner cylindrical surface dimensioned to receive the pipette coupling portion of the adaptor 310 in a friction fit.

The kit also comprises an adaptor 310, as described with reference to FIGS. 5a and 5b, a syringe body 312, and plunger 314, a reagent container 316 containing a detection buffer. The syringe body 312 and the plunger 314 are both configured to couple to the pipette coupling portion of the adaptor 310. The bottom end of the syringe body 312 comprises a compliant sealing material 313. An output opening of the syringe body, formed at a bottom end of the compliant material 313, is sealed by a glass bead as described with reference to the reagent input port of FIG. 10a. The kit may also include containers filled with various required reagents and buffers, and one or pipettes, which are not shown and may vary depending on the test to be performed.

The kit can be used in the following method. The adaptor 310 is coupled to an air-piston apparatus on a transport apparatus. The adaptor is then moved to couple to the cap 308. The cap 308 is removed from the input port 304 by the adaptor and is struck of the adaptor at a different location. A pipette is then coupled to the adaptor and used to transfer a sample to input port 304. The sample then falls into the processing chamber 302 and mixes with the solid reagent, which is an enzyme that allows for the amplification of nucleic acids. The pipette is then struck off the adaptor and the adaptor moved to couple to the syringe body 312. The syringe body 312 is then moved to the input port 308 and the compliant material seals the input port 308. The sample is then incubated in the processing chamber to amplify the nucleic acids. During amplification the adaptor is removed from the syringe body 312. The syringe body remains coupled to the input port 304 because latches 322 on the syringe body engage recesses 325 formed on the input port 304. The adaptor 310 is then coupled to a pipette and the pipette is used to transfer the detection regent from the container 316 to the syringe body 312. The detection reagent is prevented from entering the processing chamber 302 by the glass bead. The pipette is then struck off the adaptor and the adaptor is coupled to the plunger 314. The plunger is then moved to couple to the syringe body 312 to cover the detection reagent without forcing it into the processing chamber 302.

Once the incubation of the sample is complete the transport apparatus pushed the adaptor and pipette down into the syringe body to force the glass bead and the detection reagent into the processing chamber. This position is shown in FIG. 12. The adaptor can then be removed from the plunger. Latches 324 on the plunger 314 engage an upper lip of the syringe body to ensure that the plunger remains attached to the syringe body and seals the processing chamber from the external environment.

After any further incubation period necessary, the lower portion, including the processing chamber, is rotated relative to the upper portion through 180° so that the processing chamber is aligned with the analysis chamber 306. The analysis chamber contains a test strip which then falls into the processing chamber so that its end is in contact with the processed sample. The processed sample is then wicked up the test strip and the results of the test are obtained by visually inspecting the test strip.

The relative rotation between the upper portion and the lower portion of the device 300 can be driven automatically. For example, protrusions 320 on the upper portion can be used to lock the upper portion in a stationary block. The processing chamber, and optionally or alternatively other downwardly extending protrusions on the lower portions, such as feature 321 in FIG. 12, can be used to lock the lower portion to a different, moving block. The moving block can be rotated using a motor connected to a controller to effect a 180° relative rotation between the upper and lower portions of the device.

It is envisaged that a complete kit to carry out both isolation and amplification and testing using an apparatus of the type shown in FIG. 1 may be sold as a single, disposable product. FIG. 13 illustrates an exemplary kit of this type. The kit comprises a first cartridge containing a waste container 403, which is sealed by an adaptor 402 of the type already described, four pipettes 404, a syringe body 408 and a plunger 406. The syringe body 408 and plunger 406 are as described with reference to FIG. 11. The kit further comprises a second cartridge 410 containing wet reagents. Tubes 414 contain detection buffer, elution buffer and wash buffer. Tube 412 contains lysis buffer. The kit comprises a third cartridge 420 that contains dry reagents. Tube 422 contains a freeze dried sphere of proteinase K, tube 424 contains a freeze dried sphere of wash reagent, tube 426 contains a sphere of gold conjugate and tube 428 contains a freeze dried reagent sphere containing DNTPs. The third cartridge also includes a column 430 of solid phase to which nucleic acid will selectively bind. The kit also includes a device 300 as described with reference to FIGS. 11 and 12. The kit may also include a sample container.

The cartridges protect the containers during transport and provide for easy handling before and after sample processing. The containers containing reagents are each provided with a piercable seal, formed from laminated foil or plastic film. During operation of the apparatus, the pipettes are used to pierce the seals in order to access the contents of the containers. The first cartridge 400 has a sliding lid 409 that ensures that the adaptor is retained in position during transport. The entire kit may be held within a sterile pouch or container prior to use.

A method of using the kit shown in FIG. 13 in an apparatus of the type shown in FIG. 1 will now be described.

Initially the appropriate containers are put into pre-assigned openings in the track. As described previously, the initial positions of the containers are not critical as long as they are known and reflected in the sequence of movements specified in the program executed by the PC 12. The sample is incubated at different temperatures during different stages of the sample processing protocol and so some containers are placed in one thermally controlled block and other in another thermally controlled block as required.

The initial processing to isolate the nucleic acid can be performed in the same manner as illustrated in FIGS. 9A-9C, up to step 188, when the isolation of the nucleic acid is essentially complete. FIGS. 14A-14B collectively show a flow diagram illustrating the further steps of the processing protocol that can be carried out using the kit of FIG. 13.

Following step 188, the pipette 4 is moved over the reagent container 428 in step 400 and the eluate is then dispensed onto the reagent sphere in step 402. The sphere is thereby rehydrated. Pipette 4 is struck off the adaptor 402 in step 404. At the same time the sample within container 428 is incubated at 76-80° C. for 7 minutes and then cooled to 45° C. within 2 minutes.

Following incubation, the adaptor is moved over and coupled to cap 308 in step 408 and removed from the input port 304. The cap is then struck off the adaptor into the top of another container and pipette 4 is reengaged in step 410. The sample is aspirated from container 428 in step 412, and moved to the input port. The sample is then dispensed into the processing chamber through the input port in step 414. Pipette 4 is struck off the adaptor in step 416 back in its original position. The adaptor is then moved to couple with syringe body 408 in step 418. The syringe body is then coupled to the input port and the adaptor removed from the syringe body in step 420. The sample is incubated at 45° C. for 60 minutes in step 422.

During this incubation, the adaptor again couples to pipette 4 in step 424. Pipette 4 is used to aspirate the detection buffer from container 414 in step 426. The detection buffer is then moved over the gold conjugate sphere container 426 and dispensed in step 428. The mixture of detection buffer and gold conjugate may be repeatedly aspirated and dispensed to ensure thorough mixing in step 432. The mixture is then aspirated from container 426 in step 434 and dispensed into the syringe in step 436. Pipette 4 is struck off the adaptor in step 438. The adaptor is coupled to plunger 406 in step 440. The plunger is moved to cover and seal with the syringe body 408 in step 442.

The plunger and adaptor are held over the syringe body until the incubation step 422 is complete. Then, in step 444, the adaptor and plunger are moved down to dispense the detection buffer from the syringe body into the processing chamber. In step 446 the processing chamber is rotated to align with the analysis chamber. The test strip then falls into the processed sample. The adaptor is removed from the plunger and then removed from the air-piston apparatus in step 448. The adaptor is placed over the waste container 403, as described with reference to FIGS. 9A-9C.

The result of the test is read in step 450 by visually inspecting the test strip.

The visual inspection of the test strip may be carried out manually or automatically. Automatic reading of the result may be particularly beneficial to provide a fully automated process, in which even notification of the test result to a patient can be automatically generated for sending by mail, email, SMS message or the like.

The result of the test is typically indicated by the appearance of one or more lines on the test strip. To provide for automated reading of the test result a camera may be provided and controlled to record an image of the test strip a predetermined period after step 446. The recorded image may be analysed to determine if particular lines on the test strip are present or not using a suitable image processing algorithm. Any suitable digital camera may be used, such as a line scan camera.

The test strip may be illuminated to provide higher contrast images of the test strip. The test strip may also be illuminated with a particular colour of light to improve contrast. For example, if the test strip provides red lines to indicate a test result, green light may be used to provide a high contrast image of the test strip. In one embodiment, the system includes an array of green light emitting diodes directed to illuminate the test strip. The system may further include a diffuser to diffuse the illuminating light before it is incident on the test strip. One or more of the walls of the analysis chamber may be configured to act as a diffuser.

The test strip may include a transparent backing paper to allow for the test strip to be illuminated from an opposite side of the test strip to the camera. This reduces the problems of reflections from the surfaces of the analysis chamber. However, a non transparent backing paper may be used and reflected light analysed.

The analysis chamber may be shaped to optimise the capture of an image of the test strip. In particular the analysis chamber may be formed with a flat viewing window and shaped so as to minimise internal reflections that might reduce image quality. Alternatively, or in addition, one surface of the analysis chamber may be formed to provide a lens.

One or more inner surfaces of the analysis chamber may be treated to reduce the formation of condensed droplets on that surface, which might make automatic reading of the test result impossible. Alternatively, or in addition, the amplification device may be operated within a heated environment to reduce condensation inside the analysis chamber.

The camera and any light source used to illuminate the test strip may be controlled by the same PC or microprocessor that is used to control the air-piston apparatus and the transport apparatus. The camera and light source can then be configured to operate at the appropriate time following the completion of the sample processing protocol.

The kit illustrated in FIG. 13 is configured to operate with an apparatus of the type shown in FIGS. 1 and 2. However, different configurations of kit and apparatus may be used. FIG. 15 is an example of a kit of the type illustrated in FIG. 13 but configured to operate with an apparatus having a circular track that is rotated to bring each track location underneath an air-piston and transport apparatus. The kit therefore comprises arcuate shaped cartridges, each having the same radius of curvature, holding the various processing components.

The kit of FIG. 15 comprises a first cartridge 500 containing a waste container 503. The waste container is shown sealed by an adaptor 502. It can be seen that in this embodiment the closure seal on the adaptor has a non-circular, generally oval shape. The first cartridge also comprises a container 514 for detection buffer, a container 516 for wash buffer, a container 518 for elution buffer and a container 512 for lysis buffer. A second cartridge 510 comprises four pipettes 504 and a syringe 508 and plunger 506 of the type described with reference to FIGS. 11, 12 and 13. A third cartridge 520 comprises a column of solid phase material 530 and an elution tube, a container 522 holding freeze-dried sphere of proteinase K, a container 524 holding a column containing a leukoreduction filter, container 526 holding a sphere of gold conjugate and container 528 holding a freeze dried reagent sphere containing PNTPs. The kit also includes a device 300 substantially as described with reference to FIGS. 11 and 12 and a sample container 540. As with the kit of FIG. 13, the individual components and reagents may be arranged in a different manner, and divided differently between cartridges (or all placed in a single cartridge) as required and to suit the sample processing protocol to be performed.

In use, the kit of FIG. 15 is placed in recesses in a rotatable track positioned beneath an air-piston apparatus and transport apparatus. The transport apparatus is only required to move towards and away from the track to engage pipettes columns and containers in the track using the adaptor, and to aspirate and dispense fluids into the pipettes, containers and columns. In this embodiment the apparatus comprises only a single track.

FIGS. 16*a* and 16*b* illustrate an additional feature of the kit shown in FIG. 15. FIG. 16*a* is a cross-section view through the cartridge 510 and in particular through the container for the syringe 508. FIG. 16*a* shows the cartridge and syringe with the adaptor positioned to partially engage with the syringe. In this position, the seal 547 on the adaptor is engaged with the syringe but seal 548 is not. The syringe 508 is retained in the cartridge 510 by a clip element 511 formed as part of the cartridge. The clip element 511 comprises a lug on the end of a flexible arm that extends from a base to the lug in the direction in which the syringe is to be removed from the cartridge. The flexible arm can flex in a direction perpendicular to the direction in which the syringe is to be removed from the cartridge. In a rest position or retaining position, as shown in FIG. 16*a*, the lug sits above the top surface of the syringe and prevents the syringe from being removed from the cartridge.

FIG. 16*b* is the same cross section view of FIG. 16*a* but with the adaptor moved down to fully engage the syringe. In this position, both seal 547 and seal 548 are engaged with an interior surface of the syringe 508. The adaptor 502 comprises a deflecting portion 550 which engages the clip element 511 when the adaptor is in the position shown in FIG. 16b and moves the clip element out of its retaining position by deflecting the flexible arm. The lug is provided with a cam surface to achieve this deflection as the deflecting portion of the adaptor moves downwards. The syringe 508 can then be withdrawn from the cartridge 510 past the deflected clip element. The deflecting portion of the adaptor is arranged to abut a top surface of the syringe and extends radially at least as far as the top surface of the syringe 508 so the clip element cannot engage any space between the deflecting portion on the adaptor and the syringe as the syringe is withdrawn from the cartridge.

Clip elements 511 are provided at a number of positions in the cartridges 500, 510, 520, as can be seen in FIG. 15. Clip elements 511 are provided for all the pipettes and columns that are to be moved by the adaptor and transport apparatus during a sample processing operation. When pipettes or columns are replaced after use, they are again retained by the clip elements 511.

The exemplary embodiments described above illustrate but are not limiting. In view of the above discussed exemplary embodiments, other embodiments consistent with the above exemplary embodiments will now be apparent to one of ordinary skill in the art.

The invention claimed is:

1. An automated system for processing a biological-sample using a pipette and a hollow column having solid-phase material therein to which nucleic acid binds, the system comprising:
   an air-piston apparatus, comprising:
      a cylinder;
      a piston movably received in the cylinder; and
      an air-piston motor coupled to the piston;
   a transport apparatus, comprising a transport motor coupled to the air-piston apparatus and configured to transport the air-piston apparatus;
   control circuitry coupled to the air-piston motor and the transport motor;
   an adaptor removably and sealingly engaged with the cylinder of the air-piston apparatus, the adaptor comprising:
      a filter preventing transfer of liquid or aerosol into the cylinder; and
      a protruding sealing ring; and
   a testing device that engages with the adaptor and amplifies a specific, isolated nucleic acid within the sample;
   wherein:
   responsive to control of the transport motor by the control circuitry, the transport apparatus moves the adaptor to engage the protruding sealing ring of the adaptor with the pipette to form a first gas-tight seal,
   responsive to control of the transport motor by the control circuitry, the transport apparatus moves the adaptor, sealed to the pipette, relative to a liquid comprising the sample,
   responsive to control by the control circuitry, the air-piston motor drives the piston in the cylinder to draw air into the cylinder and draw the liquid into the pipette via the adaptor,
   responsive to control by the control circuitry, the air-piston motor drives the piston in the cylinder to expel air from the cylinder and expel the liquid from the pipette into the column via the adaptor,
   responsive to control of the transport motor by the control circuitry, the transport apparatus disengages the adaptor from the pipette,
   responsive to control of the transport motor by the control circuitry, the transport apparatus moves the adaptor to engage the protruding sealing ring of the adaptor with the column having the solid-phase material therein to form a second gas-tight seal, and
   responsive to control by the control circuitry, the air-piston motor drives the piston in the cylinder to expel air from the cylinder through the adaptor to push the liquid in the column into the solid phase material.

2. The automated system according to claim 1, wherein, responsive to control by the control circuitry, the air-piston motor drives the piston to expel the air from the cylinder through the adaptor at a pressure greater than atmospheric pressure.

3. The automated system according to claim 1, wherein the adaptor comprises lugs, the system further comprising an adaptor lock or striker plate affixed to the air-piston apparatus, wherein the adaptor lock or striker plate engages the lugs on the adaptor to retain the adaptor in engagement with the air-piston apparatus.

4. The automated system according to claim 1, wherein the adaptor comprises a protrusion or recess, the system further comprising a striker plate movably coupled to the air-piston apparatus and fitting around the protrusion or recess on the adaptor such that movement of the striker plate relative to the air-piston apparatus can push the pipette off the adaptor or push the column off the adaptor.

5. The automated system according to claim 1, wherein, responsive to control of the transport motor by the control circuitry, the transport apparatus sealingly couples the adaptor with each pipette of a plurality of pipettes in turn.

6. The automated system according to claim 1, wherein the testing device comprises:
   a housing having an input port for receiving the sample and one or more reagents;
   a processing chamber for receiving the sample and having a first opening;
   an analysis chamber containing a test strip for analysing the sample after processing, the analysis chamber having a second opening;
   the processing chamber being movable relative to the analysis chamber and the input port to enable communication between the processing chamber and the input port when the first opening is disposed in an overlapping relationship with the input port and communication between the processing chamber and the analysis chamber when the first opening is disposed in an overlapping relationship with the second opening;
   a sealing cap for sealing the input port prior to processing of the sample, the sealing cap being configured to engage the adaptor; and
   a sealing element for sealing the processing chamber and the analysis chamber during processing of the sample.

7. The automated system according to claim 6, wherein the sealing cap comprises a sealing portion for sealing engagement with the input port and an engagement portion for engagement with the adaptor.

8. The automated system according to claim 2, wherein the pressure is between 0.2 and 2 bar above atmospheric pressure.

9. The automated system according to claim 8, wherein the pressure is between 0.4 and 1 bar above atmospheric pressure.

10. The automated system according to claim 9, wherein the pressure is between 0.5 and 0.6 bar above atmospheric pressure.

11. The automated system according to claim 1, wherein:
   the transport apparatus further comprises a transport column coupled to the air-piston apparatus, and the transport motor comprises a first motor coupled to the transport column and configured to transport the air-piston in a first direction.

12. The automated system according to claim 11, wherein the transport motor further comprises a second motor coupled to the transport column and configured to transport the air-piston in a second direction.

13. A method for automated processing of a biological sample using a pipette and a hollow column having solid-phase material therein to which nucleic acid binds, the method comprising:
providing an air-piston apparatus, comprising:
a cylinder;
a piston movably received in the cylinder; and
an air-piston motor coupled to the piston;
providing a transport apparatus, comprising a transport motor coupled to the air-piston apparatus and configured to transport the air-piston apparatus;
providing control circuitry coupled to the air-piston motor and the transport motor;
providing an adaptor removably and sealingly engaged with the cylinder of the air-piston apparatus, the adaptor comprising:
a filter preventing transfer of liquid or aerosol into the cylinder; and
a protruding sealing ring;
moving, by the transport apparatus responsive to control of the transport motor by the control circuitry, the adaptor to engage the protruding sealing ring of the adaptor with the pipette to form a first gas-tight seal;
moving, by the transport apparatus responsive to control of the transport motor by the control circuitry, the adaptor, sealed to the pipette, relative to a liquid comprising the sample;
driving, by the air-piston motor responsive to control by the control circuitry, the piston in the cylinder to draw air into the cylinder and draw the liquid into the pipette via the adaptor;
driving, by the air-piston motor responsive to control by the control circuitry, the piston in the cylinder to expel air from the cylinder and expel the liquid from the pipette into the column via the adaptor;
disengaging, by the transport apparatus responsive to control of at the transport motor by the control circuitry, the adaptor from the pipette;
moving, by the transport apparatus responsive to control of the transport motor by the control circuitry, the adaptor to engage the protruding sealing ring of the adaptor with the column having the solid phase material therein to form a second gas-tight seal;
driving, by the air-piston motor responsive to control the control circuitry, the piston in the cylinder to expel air from the cylinder through the adaptor to push the liquid in the column into the solid phase material; and
providing a testing device configured to amplify a specific nucleic acid within the sample, wherein the adaptor is engageable with the testing device.

14. The method according to claim 13, wherein, responsive to control by the control circuitry, the air-piston motor drives the piston to expel the air from the cylinder through the adaptor at a pressure greater than atmospheric pressure.

15. The method according to claim 14, wherein the pressure is between 0.2 and 2 bar above atmospheric pressure.

16. The method according to claim 15, wherein the pressure is between 0.4 and 1 bar above atmospheric pressure.

17. The method according to claim 16, wherein the pressure is between 0.5 and 0.6 bar above atmospheric pressure.

18. The method according to claim 13, wherein the adaptor comprises lugs, the system further comprising an adaptor lock or striker plate affixed to the air-piston apparatus, wherein the adaptor lock or striker plate engages the lugs on the adaptor to retain the adaptor in engagement with the air-piston apparatus.

19. The method according to claim 13, wherein the adaptor comprises a protrusion or recess, the system further comprising a striker plate movably coupled to the air-piston apparatus and fitting around the protrusion or recess on the adaptor such that movement of the striker plate relative to the air-piston apparatus can push the pipette off the adaptor or push the column off the adaptor.

20. The method according to claim 13, wherein, responsive to control of the transport motor by the control circuitry, the transport apparatus sealingly couples the adaptor with each pipette of a plurality of pipettes in turn.

21. The method according to claim 20, wherein the testing device comprises:
a housing having an input port for receiving the sample and one or more reagents;
a processing chamber for receiving the sample and having a first opening;
an analysis chamber containing a test strip for analysing the sample after processing, the analysis chamber having a second opening;
the processing chamber being movable relative to the analysis chamber and the input port to enable communication between the processing chamber and the input port when the first opening is disposed in an overlapping relationship with the input port and communication between the processing chamber and the analysis chamber when the first opening is disposed in an overlapping relationship with the second opening;
a sealing cap for sealing the input port prior to processing of the sample, the sealing cap being configured to engage the adaptor; and
a sealing element for sealing the processing chamber and the analysis chamber during processing of the sample.

22. The method according to claim 13, wherein:
the transport apparatus further comprises a transport column coupled to the air-piston apparatus, and
the transport motor comprises a first motor coupled to the transport column and configured to transport the air-piston in a first direction responsive to control by the control circuitry.

23. The method according to claim 22, wherein the transport motor further comprises a second motor coupled to the transport column and configured to transport the air-piston in a second direction responsive to control by the control circuitry.

* * * * *